United States Patent
Sørum

(10) Patent No.: US 11,266,168 B2
(45) Date of Patent: Mar. 8, 2022

(54) PROBIOTIC BACTERIA FOR FISH

(71) Applicant: PREVIWO AS, Kjeller (NO)

(72) Inventor: Henning Sørum, Oslo (NO)

(73) Assignee: PREVIWO AS, Kjeller (NO)

( * ) Notice: Subject to any disclaimer, the term of this patent is extended or adjusted under 35 U.S.C. 154(b) by 427 days.

(21) Appl. No.: 16/315,947

(22) PCT Filed: Jul. 7, 2017

(86) PCT No.: PCT/EP2017/067169
§ 371 (c)(1),
(2) Date: Jan. 7, 2019

(87) PCT Pub. No.: WO2018/007632
PCT Pub. Date: Jan. 11, 2018

(65) Prior Publication Data
US 2020/0236975 A1  Jul. 30, 2020

(30) Foreign Application Priority Data
Jul. 8, 2016 (NO) .................................. 20161144

(51) Int. Cl.
*A23K 50/80* (2016.01)
*A23K 10/18* (2016.01)
*A01K 61/13* (2017.01)

(52) U.S. Cl.
CPC .............. *A23K 50/80* (2016.05); *A01K 61/13* (2017.01); *A23K 10/18* (2016.05)

(58) Field of Classification Search
CPC ........ A23K 50/80; A23K 10/18; A01K 61/13; Y02A 40/81; A61K 2035/115; A61K 2039/552; A61K 39/107; A61K 39/00; A61K 35/741; A61K 39/02; C12R 2001/63; C12N 1/205; C07K 14/195; C07K 14/28
See application file for complete search history.

(56) References Cited

FOREIGN PATENT DOCUMENTS

| NO | 20120561 A1 | 11/2013 |
| WO | WO/2013/171236 | 11/2013 |
| WO | WO 2015/074946 | 5/2015 |
| WO | WO 2018/007632 | 1/2018 |

OTHER PUBLICATIONS

International Search Report and Written Opinion of related PCT/EP2017/067169, dated Oct. 5, 2017, 13 pages.
Norwegian Search Report of related No. 20161144, dated Dec. 16, 2012, 2 pages.
(Continued)

*Primary Examiner* — Nikki H. Dees
*Assistant Examiner* — Jeffrey D Benson
(74) *Attorney, Agent, or Firm* — Casimir Jones, S.C.; Tanya A. Arenson

(57) ABSTRACT

A method for increasing the weight and growth rate of fish, preferably Salmonidae, and for preventing and/or treating microbial infections, comprising the steps of a) adding one or more species of probiotic bacteria to water, wherein the species of bacteria comprises or consists of *Aliivibrio njordis*, *Aliivibrio balderis* and/or *Aliivibrio nannie*; and b) exposing the fish to the water containing the one or more species of probiotic bacteria. Preferably, the bacterial strains *Aliivibrio njordis* strain B1-25, 8-1/2013 mandib V11, *Aliivibrio balderis* B1-24, 18-1/2013 kidn V12 and/or *Aliivibrio nannie* B8-24, 313/2013 kidn V13 are used.

8 Claims, 12 Drawing Sheets

(56) References Cited

OTHER PUBLICATIONS

Balcazar et al., "The role of probiotics in aquaculture." Vet Microbiol. May 31, 2006;114(3-4):173-86.
Cruze et al., "Use of probiotics in aquaculture." ISRN microbiology, 2012, 13 pages.
Godoy et al.,"High variability of levels of Aliivibrio and lactic acid bacteria in the intestinal microbiota of farmed Atlantic salmon *Salmo salar* L." Annals of Microbiology Dec. 2015, vol. 65, Issue 4, pp. 2343-2353.
Ibrahem et al., "Evolution of probiotics in aquatic world: potential effects, the current status in Egypt and recent prospectives." Journal of advanced research 6.6 (2015): 765-791.
Newaj-Fyzul et al., "Developments in the use of probiotics for disease control in aquaculture. Aquaculture 431 (2014): 1-11."
Pandiyan et al., "Probiotics in aquaculture." Drug Invention Today 5.1 (2013): 55-59.
Verschuere et al.,"Probiotic bacteria as biological control agents in aquaculture." Microbiol Mol Biol Rev. Dec. 2000;64(4):655-71.

PROBIOTIC BACTERIA FOR FISH

CROSS REFERENCE TO RELATED APPLICATIONS

The present application is a Section 371 U.S. national stage entry of pending International Patent Application No. PCT/EP2017/067169, international filing date Jul. 7, 2017, which claims priority to NO Patent Application No. 20161144, filed Jul. 8, 2016 the contents of which are incorporated by reference in their entireties.

The present document is directed to fish farming. More particularly, the present document is directed to means and methods for increasing the growth of fish by using probiotic bacteria. The present document also discloses means and methods for treating and/or preventing microbial infections, such as bacterial infections, in fish by the use of probiotic bacteria.

BACKGROUND OF THE INVENTION

Fish farming involves raising fish in tanks or enclosures. In aquaculture, freshwater and saltwater populations, such as fish, crustaceans and shellfish, are raised under controlled conditions. Mariculture is a sub-branch of aquaculture where marine organisms are cultivated in the open ocean or an enclosed section of the ocean, or alternatively in ponds, tanks and the like filled with seawater.

The growth and health of fish raised by intensive aquaculture is dependent on that sufficient oxygen and clean water with optimal levels of carbon dioxide, ammonia and with feasible pH can be provided. Also, a sufficient amount of feed with a high content of protein and a well-balanced supply of amino acids is crucial to obtain a commercially durable result. Attempts to increase the growth of farmed fish have generally focused on changing the contents of the feed used.

Farmed fish are often contained at high concentrations which increase the risk for infections by e.g. parasites such as fish lice, intestinal worms, fungi, virus and bacteria. In order to control such infections, the fish farming industry often relies on the use of antibiotics and chemical control agents, which is undesirable e.g. due to the spread of these toxic agents to the environment and the fear for antibiotic resistance development in the society.

A particular problem with farmed fish is bacteria which cause wounds and ulcers in the skin of the fish which reduce the quality of the slaughtered fish even if it survives the infection because of scar tissue and which causes suffering to the fish. The ulcer bacteria also cause septicemia that increases the percentage of fish that die because of the infection. Examples of bacteria which have been associated with such disease are *M. viscose, Bizionia piscinecroseptica, Aliivibrio friggiae, Tenacibaculum dicentrarchi, Aliivibrio wodanis*. The creation of wounds on the skin of the fish is also expected to present a route for entry for other pathogenic organisms. Acute bacterial infections in farmed fish that causes outbreaks with high loss in the population in a limited time creates a high concentration of bacterial pathogens that causes effective spread of the infection between the individuals in the population. Some of the fish pathogens causing epidemic outbreaks are *Aliivibrio salmonicida, Aeromonas salmonicida, Vibrio anguillarum, Edwardsiella piscicida,* and *Aeromonas hydrophila*. The ports of infection for bacterial pathogens are not well studied but both the gills, the intestine and the skin are considered important.

Vaccination has been used or proposed as a means for treating and preventing these kinds of bacterial infections. Antibiotic treatment of outbreaks of acute bacterial infections is often used in many countries. Routinely use of antibiotics often causes antibiotic resistant bacterial fish pathogens.

Due to the above discussed problems among others, fish farming industries often face a high loss of the farmed fish with negative economic consequences for the fish farmer. Thus, increasing the survival of the fish and increasing the net output in relation to the amount of feed used is highly desirable.

The object of the present invention is to overcome or at least mitigate some of the problems associated with the prior art.

SUMMARY OF INVENTION

The above problems have now been mitigated or overcome by the isolation and characterization of three novel species of the *Aliivibrio* genus, namely *Aliivibrio njordis, Aliiivibrio balderis* and *Aliivibrio nannie* which have been shown to have a probiotic effect on fish, such as fish of the family Salmonidae and marine cleaner fish as wrasses and lump suckers. The bacteria of the species *Aliivibrio njordis, Aliiivibrio balderis* and *Aliivibrio nannie* may in the context of the present document be referred to as "the probiotic bacteria", "the probiotic bacterium" and the like.

The present document is thus directed to a method for increasing the growth rate and/or weight of fish by administering the probiotic bacteria to the fish, such as by topical administration (i.e. administration by dipping, bathing or similar immersion techniques), administration via the gills and/or the intestine.

The present document is thus also directed to a method for increasing the weight of fish, said method comprising the steps of
  a) adding one or more species of probiotic bacteria to water, wherein the species of bacteria comprises or consists of *Aliivibrio njordis, Aliivibrio balderis* and/or *Aliivibrio nannie*; and
  b) exposing the fish to the water containing the one or more species of probiotic bacteria.

The present document is thus also directed to a method for increasing the growth rate of fish, said method comprising the steps of
  a) adding one or more species of probiotic bacteria to water, wherein the species of bacteria comprises or consists of *Aliivibrio njordis, Aliivibrio balderis* and/or *Aliivibrio nannie*; and
  b) exposing the fish to the water containing the one or more species of probiotic bacteria.

The present document is further directed to a method for treating and/or preventing a microbial infection in fish by administering the probiotic bacteria to the fish such as by topical administration, administration via the gills and/or the intestine.

The present document is thus further also directed to a method for treating and/or preventing a microbial infection in fish, said method comprising the steps of
  a) adding one or more species of probiotic bacteria to water, wherein the species of probiotic bacteria comprises or consists of *Aliivibrio njordis, Aliivibrio balderis* and/or *Aliivibrio nannie* and any combination thereof; and
  b) exposing the fish to the water containing the one or more species of probiotic bacteria.

The present document is further directed to a probiotic bacterium of the species *Aliivibrio njordis, Aliivibrio balderis* and/or *Aliivibrio nannie* for use in the treatment and/or prevention of a microbial infection in fish.

The present document is additionally directed to the use of a probiotic bacterium of the species *Aliivibrio njordis, Aliivibrio balderis* and/or *Aliivibrio nannie* for the manufacture of a medicament for the treatment and/or prevention of a microbial infection.

The present document is also directed to a probiotic bacterium of the species *Aliivibrio njordis, Aliivibrio balderis* and/or *Aliivibrio nannie* for use in the treatment and/or prevention of a microbial infection in fish and for the simultaneous use in increasing the growth rate and/or weight of said fish.

The present document is also directed to the use of a probiotic bacterium of the species *Aliivibrio njordis, Aliivibrio balderis* and/or *Aliivibrio nannie* for the manufacture of a medicament for the treatment and/or prevention of a microbial infection in fish and simultaneously increasing the growth rate and/or weight of said fish.

The present document is also directed to a method for the treatment and/or prevention of a microbial infection in fish and simultaneously increasing the growth rate and/or weight of fish, said method comprising the steps of
 a) adding one or more species of probiotic bacteria to water, wherein the species of bacteria comprises or consists of *Aliivibrio njordis, Aliivibrio balderis* and/or *Aliivibrio nannie*; and
 b) exposing the fish to the water containing the one or more species of probiotic bacteria.

The microbial infection which may be treated and/or prevented by the probiotic bacteria of the present document may be a bacterial infection. The bacterial infection may be an infection causing wounds, ulcers and/or lesions on the skin of the fish, and/or septicaemia. Examples of bacteria which infection may be treated and/or prevented by the probiotic bacteria of the present document include, but are not limited to bacteria selected from the group comprising of *M. viscose, Bizionia piscinecroseptica, Aliivibrio friggiae, Tenacibaculum dicentrarchi, Aliivibrio wodanis, Aliivibrio salmonicida, Aeromonas salmonicida, Vibrio anguillarum, Edwardsiella piscicida, Aeromonas hydrophila, Flavobacterium psychrophilum,* and *Aliivibrio* salmonicida.

The probiotic bacteria may be administered to the fish by
a) adding one or more species of a probiotic bacterium to water; and
b) exposing the fish to the water containing the one or more species of a probiotic bacterium.

The bacterial species may be used alone or in any combination. Also, more than one strain of each species may be used. Further, if more than one species and/or strain is used, any ratio between the different species and/or strains may be used. Typically the different bacterial species and/or strains are used in a ratio of 1:10 to 10:1 or in equal amounts.

When the probiotic bacteria of the present document are administered to fish by exposing the fish to water containing the probiotic bacteria, the water may have a salt concentration from 0 to about 4% by weight, such as about 0.5 to about 4%, such as about 2 to about 4% by weight. The water may e.g. be natural sea water. As an example freshwater can be added culture with probiotic bacteria in high enough concentration to keep the salt concentration above zero from the higher salt concentration in the culturing media.

The fish may be exposed to the probiotic bacteria for a time period of 1 second to 5 hours, such as 1 second to 2 hours, such as 1 second to 1 hour, such as 30 seconds to 1 hour or 1 minute to 30 minutes when exposed via bathing in water containing the probiotic bacteria. The bathing may be repeated one or more times, such as 1-20 times. The fish may e.g. be exposed to the bacteria 1-20 times, 1-10 times, 1-5 times, 1-4 times, 1-3 times or 1-2 times.

The fish that may be administered with the probiotic bacteria are fish of the family Salmonidae, such as salmon, trout, chars, freshwater whitefishes or graylings. The fish may also be marine cleaner fish as wrasses and lump suckers. The fish may be farmed fish.

The present document is also directed to an exemplary strain of a probiotic composition comprising one or more of a probiotic bacterium selected from the group consisting of *Aliivibrio njordis, Aliivibrio balderis* and *Aliivibrio nannie*.

The present document is also directed to an isolated and biologically pure exemplary strain of the novel species *Aliivibrio njordis* which strain is the strain *Aliivibrio njordis* B1-25, 18-1/2013 mandib V11, which has been deposited at National Collection of Industrial and Marine Bacteria and has been assigned accession number NCIMB 42593.

The present document is also directed to an isolated and biologically pure exemplary strain of the novel species *Aliivibrio balderis* which strain is *Aliivibrio balderis* B1-24, 18-1/2013 kidn V12, which has been deposited at National Collection of Industrial and Marine Bacteria and has been assigned accession number NCIMB 42592.

The present document is also directed to an isolated and biologically pure exemplary strain of the novel species *Aliivibrio nannie* which strain is is *Aliivibrio nannie* B8-24, 313/2013 kidn V13, which has been deposited at National Collection of Industrial and Marine Bacteria and has been assigned accession number NCIMB 42594.

When the present document refers to a bacterium of the species *Aliivibrio njordis, Aliivibrio balderis* and/or *Aliivibrio nannie* it is understood that said bacterium has a biological activity comparable to the above respective deposited exemplary strains of said *Aliivibrio njordis, Aliivibrio balderis* and/or *Aliivibrio nannie* bacteria.

Other features and advantages of the invention will be apparent from the following detailed description, drawings, examples, and from the claims.

Definitions

"Salmonidae" is a family of ray-finned fish, which is the only living family currently placed in the order Salmoniformes. These are also referred to herein as salmonids. Salmonidae includes salmon, trout, chars, freshwater whitefishes and graylings.

A "culture" includes all forms of culture, both in broth, on agar and in any other media like eukaryotic cell cultures, eukaryotic/animal/fish tissue within research animals or any other physical measure. A "single culture" refers to a culture containing only one bacterial strain, i.e. a pure culture. A "mixed culture" refers to a culture wherein two or more bacterial strains, species and/or general are grown together. The temperature and the salt concentration (e.g. NaCl) conditions for each culture can be determined separately, depending on the circumstances and the materials used.

"Winter ulcer" is a disease which is characterized by skin ulcers that develop from skin swellings into open ulcers and later into larger ulcerated skin areas where the underlying muscle tissue is exposed and often destroyed by necrosis. Winter ulcer is mainly occurring at sea water temperatures from <6 to 15° C., such as from <6 to 8° C. At these temperatures *M. viscose* is most clinically active and aggressively attacks the skin of the fish directly creating small ulcers, as well as infect the fish septicemically mainly through the gill epithelium (Lunder et al. 1995, Løvoll et al. 2009, Karlsen et al. 2012).

By the terms wound, ulcer, lesion and the like is in the context of the present document intended damages to the skin tissue. Such injuries may be caused by either trauma and/or by microbial infection, such as bacterial infection.

By the term "skin" and the like is intended the outer covering of a body. The skin of a fish generally comprises an outer covering of scales under which the epidermis and dermis are placed. A wound, ulcer or lesion may affect all three of these layers or only one or two of the outer layers.

"Fish farming", "farmed fish" and the like expressions refer to the commercial raising of fish. Often such fish farming takes place in enclosed spaces, such as cages, tanks or ponds.

"Bizioniosis" is a disease characterized by tail- and fin rot, infection on the tip of the mandibular, in particular, but also on the tip if the maxilla which may spread along the mandibula caudally, eye infection, ulcers behind the pectoral fins and alongside the body, and/or septicaemia (see WO 2015/074943). In particular, bizioniosis is characterized by these symptoms being caused by bacteria of the genus *Bizionia*, such as *Bizionia piscinecroseptica*, such as *Bizionia piscinecroseptica* 130524K2F7.

"Friggiosis" is a disease characterized by septicemia (in particular with a high number of bacteria in head kidney and liver), mottled bleedings in a fatty degenerated liver, ascites in the abdomen, ulcers on the skin (such as behind the pectoral fins or spread out on the body) but often no or fewer ulcers on the body than compared to ulcers in winter ulcer and wodanosis, eye infection (which may lead to puncture of the eye), an infection of the tip of the mandibula and/or the tip of the maxilla (see WO 2015/074946). Friggiosis may be characterized by being caused by bacteria of the novel species *Aliivibrio friggiae*, such as *Aliivibrio friggiae* 130206K7F2 506.

Flexibacteriosis (marine) is caused by *Tenacibaculum maritimum* (formerly, *Cytophaga marina*, *Flexibacter marinus* and *F. maritimus*) and for Atlantic salmon *Tenacibaculum dicentrarchi* is the most common cause of fin rot and ulcers among bacteria in genus *Tenacibaculum*. Several other names as gliding bacterial diseases of sea fish, eroded mouth syndrome and black patch necrosis has been used to designate the disease caused by this bacterium. Marine flexibacteriosis is widely distributed in cultured and wild fish in Europe, Japan, North America and Australia. The disease has been reported among the cultured fish as turbot, sole, gilthead seabream, seabass, red seabream, black seabream (*Acanthopagrus schlegeli*), flounder and salmonids. Although both adults and juveniles may be affected by marine flexibacteriosis, younger fish suffer a more severe form of the disease. Increased prevalence and severity of the disease is observed at higher temperatures (above 15° C.). The disease is influenced by many environmental (stress) and host-related factors (skin condition). In general, the affected fish have eroded and haemorrhagic mouth, ulcerative skin lesions, frayed fins and tail rot. A systemic disease can occur involving different internal organs. The loss of the epithelial fish surface, a typical change of the disease, is probably portal of entry for other bacterial or parasitic pathogens (Toranzo et al. 2005).

Bacterial cold water disease (BCWD) (Cipriano and Holt 2005) Fish infected with typical BCWD have lesions on the skin and fins. Fins may appear, split, torn, ragged, frayed and may even be eroded totally. Affected fish are often lethargic and stop feeding. Infection may spread septicemically. Salmonid fish can develop a chronic form of BCWD-following recovery from typical BCWD. It is characterised by "corkscrew" swimming, blackened tails and spinal deformities. *Flavobacterium psychrophilum* is considered to be the causative agent of both BCWD and Rainbow trout fry syndrome.

Rainbow trout fry syndrome is an acute disease with high mortality rates. Infected fish may show signs of lethargy, inappetance and exopthalmos before death (Nematollahi et al. 2003). The clinical signs of *F. psychrophilum* infections as well as the mortality rate depend on the size of the affected fish. In coho salmon, which are highly susceptible, the mortalities can be as high as 50%. In fingerlings, a dark pigmentation on one side of the body and erosion of the peduncle area with concomitant exposure of the spinal cord and tail loss are common findings.

Wodanosis is characterized by septicemic infection resulting in ascites, mottled liver, swollen spleen, skin ulcers, and/or fin rot typically on the bases of the tail fin and back fin. Wodanosis may be caused by *Aliivibrio wodanis*. Wodanosis is further described in WO2013/171236.

Cold-water vibriosis in Atlantic salmon may be caused by the gram-negative bacterium *Aliivibrio salmonicida*.

DETAILED DESCRIPTION

Figure 1:
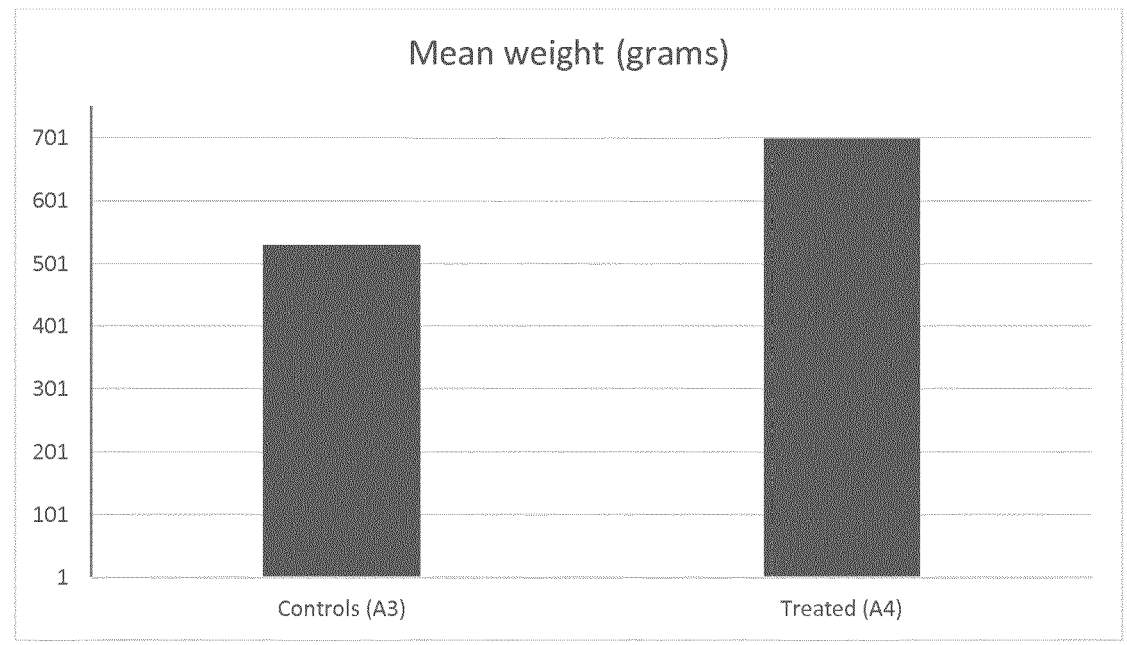
FIG. 1: mean weight of smolts bathed in equal amounts of *Aliivibrio njordis* (B1-25, 18-1/2013 mandib VI1), *Aliivibrio balderis* (B1-24, 18-1/2013 kidn VI2) and *Aliivibrio nannie* (B8-24, 31-3/2013 kidn VI3) according to Example 1.

The present document is directed to increasing the growth rate and/or weight and/or improving the health of farmed fish by the use of novel probiotic bacteria of the genus *Aliivibrio* which typically are administered via exposure of the fish to water to which the probiotic bacteria have been added. The probiotic bacteria disclosed herein for the first time are of the novel species *Aliivibrio njordis, Aliivibrio balderis* and *Aliivibrio nannie*. Three exemplary novel species of *Aliivibrio* have been isolated in Norway and deposited according to the Budapest Treaty on Jun. 17, 2016, at the National Collection of Industrial and Marine Bacteria (Ferguson Building, Craibstone Estate, Bucksburn, Aberdeen, AB21 9YA, Scotland, United Kingdom). These exemplary strains are *A. njordis* (B1-25, 18-1/2013 mandib V11) which is given the accession number NCIMB 42593, *Aliivibrio balderis* (B1-24, 18-1/2013 kidn V12) which is given accession number NCIMB 42592, and *Aliivibrio nannie* (B8-24, 313/2013 kidn V13) which is give accession number NCIMB 42594.

Probiotics have previously been used in fish farming mainly as a food supplement for farmed fish like salmonids. Administration of probiotic bacteria through bathing procedures has mainly been applied for shrimp, shellfish and early feeding and even pre-feeding stages of fin-fish like halibut and Atlantic cod. However, it has now been found that it is possible to administer probiotic bacteria via the water the fish is contained in to get a beneficial effect on the fish, such as Atlantic salmon, even in the smolt stage.

Although it has previously been demonstrated that pathogenic bacteria, such as *Moritella viscose* and *Affivibrio salmonicida* enter fish via the skin as the main port of infection in addition to uptake through the intestine and gills, it has not previously been demonstrated that the growth of the fish (rate of weight increase) can be increased by topical administration (i.e. for instance as by immersion as dipping or bathing) of probiotic bacteria to the skin of the fish. Further, it has not previously been demonstrated that wound formation on the skin of the fish can be treated and/or prevented by the topical administration of probiotic bacteria to the skin of the fish. In addition to the topical effect, the probiotic bacteria is passing through the skin of the fish as their close genetic relatives that are pathogens are doing, like *Affivibrio salmonicida*. An effect from this entrance in the fish is that the probiotic bacteria also can prevent septicemic infections in the fish.

The present document for the first time demonstrates that it is possible to administer probiotic bacteria to fish, such as smolts of Atlantic salmon, by providing the bacteria to water and exposing the fish to the bacteria-containing water. By this administration, the main route of entry of the probiotic bacteria is via the skin of the fish (i.e. topically).

Two main effects have been observed to occur after the administration of the probiotic bacteria by exposure to the probiotic bacteria via their surrounding water. One is the non-medical effect of an increased growth of the fish, as demonstrated by an increase in weight as compared to untreated fish. The other is the medical effect of prevention and/or treatment of skin wounds (ulcers, lesions), as demonstrated by a reduced number of wounds of the skin as compared to untreated fish. Such beneficial effects have previously not been demonstrated to occur after the administration of probiotic bacteria by adding probiotic bacteria to water and exposing fish to the bacteria-containing water.

The present document discloses three novel bacterial species, which all have been found to beneficially affect fish when administered via the fishes' surrounding water. These bacterial species are *Affivibrio njordis, Affivibrio balderis* and *Affivibrio nannie*, which are further disclosed in the below. In the context of the present document, these bacteria may be referred to as the probiotic bacteria.

The bacteria may be administered to the fish by exposing the fish to water to which the probiotic bacteria have been added. Such administration results in a topical administration of the probiotic bacteria to the fish. However, other means and routes for administration may also be used.

The probiotic bacteria disclosed herein may be administered separately or in any combination of two or more of the species and/or different strains of the different species. All three species of probiotic bacteria disclosed herein have the beneficial effects on growth (weight increase) and prevention/treatment of microbial infections, independently on whether or not they are used separately or in any combination. For example, *A. njordis, A. balderis* or *A. nannie* may be used alone. Also, *A. njordis* may be used in combination with *A. balderis*, in combination with *A. nannie* or in combination with *A. balderis* and *A. nannie*. Further, *A. balderis* may be used in combination with *A. nannie*. Bacteria of the different genera and/or different strains may be used at any relative ratio. However, typically, the ratio is about 1:10 to about 10:1 between any two species/strains when the bacteria are used in combination. For example, the ratio between any two species/strains when the bacteria are used in combination may be 1:4 to 4:1, 1:3 to 3:1, 1:2 to 2:1 or 1:1. However, it may also be about 1:100 to 100:1.

In order to administer the probiotic bacteria to the fish, the probiotic bacteria are cultured in a suitable manner and then e.g. added to water whereafter the fish are exposed to the bacteria-containing water, i.e. bathing the fish in the water. The water to which the bacteria are added may be the water that the fish are already contained in or may be water in another tank, cage or the like to which the fish are transferred. The water is typically the same kind of water that the fish are contained in depending on their growth stage. For e.g. salmon at the post smolt stage, the water is typically natural sea water. However, it is also possible to transfer the fish to another kind of water during the treatment. For example, salmon at the pre smolt stage, which live in fresh water, may be transferred to salt water, such as natural seawater, during the exposure to the probiotic bacteria and then moved back to the fresh water. The water to which the bacteria are added typically has a salinity of about 0.5 to about 4 weight %, such as about 2 to about 4 weight %, although the water may also be fresh water which has a much lower salinity. It is thus possible to use already propagated live cells to bath fish at lower salt concentrations down to fresh water at typical shorter time intervals not killing the probiotic bacteria.

The fish are exposed to the bathing water containing the probiotic bacteria for a time sufficient for enough bacteria to be administered to the fish to obtain the desired effects.

This time will depend on e.g. the concentration of bacteria used, the type and status of the fish that are to be exposed etc. Typically, an exposure time of a few seconds to a couple of hours may be used, such as 1 second to 5 hours, such as 1 second to 2 hours, such as 1 second to 1 hour, such as 30 seconds to 1 hour or 1 minute to 30 minutes. Increasing the concentration of bacteria in the water will generally decrease the exposure time needed.

The fish may be exposed to the probiotic bacteria a single time or the exposure may be repeated one or more times with different time intervals.

The total concentration of added probiotic bacteria in the bathing water is typically in the range of about $10^4$ to $10^8$ CFU/ml, such as $10^5$ to $10^7$, when applying a bath for a short single treatment interval, such as a bathing lasting for about 15 to 60 minutes. If the fish are rather to be dipped in a probiotic bath, the bacterial concentration may be increased such as to $10^7$ to $10^{12}$ CFU/ml. Bacterial cultures prepared in fermenters may have a concentration of ca $10^{13}$ CFU/ml. A dilution of ca 1:100 to 1:600 of the prepared bacterial culture may be suitable for application by bathing and a dilution of ca 1:10 for application by dipping. Adding probiotic bacteria at repeated intervals at lower concentrations down to the natural level in seawater may be beneficial to the bathed fish. A continuous infusion of probiotic bacteria at lower levels of concentration down to one cell/ml water may be beneficial to the fish.

The probiotic bacteria may be added to the water with or without their used growth medium. If the bacteria are to be added without their used growth medium, the bacterial cells may be separated from the growth medium e.g. by centrifugation or filtering and thereafter resuspended in fresh growth medium or a suitable buffer (such as phosphate buffered saline) or salt solution (such as a sodium salt solution).

It is also possible to use freeze-dried probiotic bacteria or recirculating aquaculture systems (RAS).

Probiotic bacteria of the different species disclosed herein and/or different strains within the same species may be mixed before addition to the water. The different species of probiotic bacteria and/or different strains within the same species may also be cultured together in the same culture. For example, all three species or in any mix of two of the species may be cultured together. It is also possible to culture two or more strains of the same species together or in combination with one or more strains of another species.

The present document is thus also directed to a probiotic composition comprising one or more of a probiotic bacterium selected from the group consisting of *Aliivibrio njordis*, *Aliivibrio balderis* and *Aliivibrio nannie*. Probiotic bacteria of the different species and/or different strains within the same species may also be added separately but to the same volume of water for the fish to be exposed to the different bacteria simultaneously. It is also possible to expose the fish to probiotic bacteria of the different species disclosed herein and/or strains of one or more of the species sequentially by adding one or more probiotic bacterial species/strains before the addition of one or more further probiotic bacterial species/strains. If such a sequential addition of the probiotic bacteria is to be used, it is possible to add the bacteria sequentially but without removing previously added bacteria or to effect removal of previously added bacteria before new bacteria are added, e.g. by exchanging the volume of bacteria containing water for new water before addition of further bacteria.

Exemplary strains of probiotic bacteria of the species *A. njordis*, *A. balderis* and *A. nannie* that may be used for the purposes of the present document are *Aliivibrio njordis* strain B1-25, 18-1/2013 mandib VI1, *Aliivibrio balderis* B1-24, 18-1/2013 kidn VI2, and *Aliivibrio nannie* B8-24, 31-3/2013 kidn VI3. The present document is however not limited to the use of these specific strains, but any strain of the three species may be used provided it has a probiotic activity similar to the respective exemplary strain of each species.

The fish that are to be exposed to the probiotic bacteria disclosed herein are any kind of fish, in particular farmed fish and more particularly fish of the family Salmonidae, such as salmon, trout, chars, freshwater whitefishes or graylings. As mentioned above, the fish may be exposed to the probiotic bacteria one or more times, e.g. during different growth stages. In addition marine fish species like the various wrasse species and lump sucker fish used as cleaner fish in controlling sea lice infestations in the marine net pens may have beneficial effects of the three probiotic bacteria since they are also infected by several of the same wound and ulcer pathogens as salmonid fish. The same will apply to many different marine species like for instance squid species.

Bacterial Strains

In the below the isolation and characterization of exemplary strains of bacteria of the species *A. njordis*, *A. balderis* and *A. nannie* is disclosed. The present document is however not limited to the use of these specific strains, but any strain of bacteria of the species *A. njordis*, *A. balderis* and *A. nannie*, which have a comparable effect in increasing the weight of fish and/or in treating/preventing microbial infection as these exemplary strains, may be used for the purposes of the present document.

*Aliivibrio njordis*

*Aliivibrio njordis* (B1-25, 18-1/2013 mandib V11) was isolated from the mandibula (lower jaw) of an Atlantic salmon that had died on 18 Jan. 2013 in an experimental tank at Solbergstrand, NIVA, Norway, using natural seawater. The isolate was grown on blood agar with 2.5% NaCl added and incubated for four days at +10° C. The colonies are typically 2-3 mm wide with a moist, even surface, a yellowish colour and non-hemolytic. The bacterial cells are gram-negative with a typical length from 2 to 5 µm and a diameter of 1 µm. The form of the cells may be coccoid to straight or comma-shaped typical *vibrio* cells. *A. njordis* utilizes $NO_3$ but are not degrading L-tryptophane, D-glucose, L-arginine, urea, esculin, gelatin or PNPG.

*Aliivibrio balderis*

*Aliivibrio balderis* (B1-24, 18-1/2013 kidn V12) was isolated from the head kidney of an Atlantic salmon that had died on 18 Jan. 2013 in an experimental tank at Solbergstrand, NIVA, Norway, using natural seawater. The isolate was grown on blood agar with 2.5% NaCl added and incubated for four days at +10° C. The colonies are typically 2-3 mm wide with a moist, even surface, a yellowish colour and non-hemolytic. The bacterial cells are gram-negative with a typical length from 2 to 5 µm and a diameter of 1 µm. The form of the cells may be coccoid to straight or comma-shaped typical *vibrio* cells. *A. balderis* utilizes $NO_3$ and are fermenting D-glucose and are degrading esculin and PNPG but are not degrading L-tryptophane, L-arginine, urea, or gelatin.

*Aliivibrio nannie*

*Aliivibrio nannie* (B8-24, 313/2013 kidn V13) was isolated from the head kidney of an Atlantic salmon that had died on 31. March 2013 in an experimental tank at Solbergstrand, NIVA, Norway, using natural seawater. The isolate was grown on blood agar with 2.5% NaCl added and incubated for four days at +10° C. The colonies are typically 2-3 mm wide with a moist, even surface, a yellowish colour and non-hemolytic. The bacterial cells are gram-negative with a typical length from 2 to 5 μm and a diameter of 1 μm. The form of the cells may be coccoid to straight or comma-shaped typical *vibrio* cells. *A. nannie* utilizes $NO_3$ and are degrading PNPG but are not degrading L-tryptophane, D-glucose, L-arginine, urea, esculin, or gelatin.

Growth of *A. njordis*, *A. balderis* and *A. nannie* The conditions for growth of the bacteria are not critical as long as viable cells are obtained.

The medium used for growing the bacteria is not critical, but any nutrient medium containing all the elements that most bacteria need for growth and which is non-selective may be used, such as Luria Broth, Trypticase Soy Agar, or Nutrient Agar.

The temperature for growing the bacteria is not critical either. Typically, the bacteria are grown at a temperature between 2 and 25° C., such as about 4 to 18° C.

The bacteria may be grown under aerobic, or microaerophilic or even anaerobic conditions. Aerobic conditions may be effected by e.g. vigorously shaking the bacterial cultures while microaerophilic conditions may be effected by e.g. carefully turning the bacterial culture flasks during growth. Growing the bacteria at both microaerophilic and aerobic conditions has been used in the experiments disclosed herein but other conditions may be preferred when the bacteria are going to be used for the purposes disclosed herein.

If bacteria of more than one species and/or strain is to be used, the bacteria may be grown separately (i.e. in single cultures) or in the same culture (i.e. in mixed cultures). If grown separately, bacteria of the different cultures may be mixed before addition to the water or the bacteria of the different cultures. The present document is thus also directed to a probiotic composition comprising one or more of a bacterium selected from the group consisting of *Aliivibrio njordis*, *Aliivibrio balderis* and *Aliivibrio nannie*. Probiotic bacteria obtained from different cultures (independently of whether single or mixed cultures) may also be added separately but to the same volume of water for the fish to be exposed to the different bacteria simultaneously.

Medical and Non-Medical Uses of the Probiotic Bacteria
Non-Medical Use of the Probiotic Bacteria The present document discloses the use of the probiotic bacteria for increasing the growth rate (weight) as compared to fish not treated with the probiotic bacteria. This effect is caused by the administration of the probiotic bacteria by exposing the fish to water to which the probiotic bacteria have been added. Without wishing to be bound by theory, it is expected that the main effect is contributed by the topical administration of the bacteria to the skin of the fish. The bacteria then traverse effectively the skin of the fish and ends up in the subcutaneous tissues and the blood vessels of the body transporting the bacteria throughout the fish body.

The present document thus is directed to a method for increasing the rate of growth (weight) of fish, said method comprising the steps of a) adding one or more species of probiotic bacteria to water, wherein the species of probiotic bacteria comprises or consists of *Aliivibrio njordis*, *Aliivibrio balderis* and/or *Aliivibrio nannie*; and b) exposing the fish to the water containing the one or more species of probiotic bacteria.

As mentioned elsewhere herein, probiotic bacteria of the three different species and different strains within such species may be used in any combination. One example of such a combination is the combination of bacteria from the species *A. njordis* and *A. balderis*. The bacterial species may thus be used alone or in different combinations of two or more species and/or strains of a species. Further details regarding the conditions during exposure of the fish to the probiotic bacteria etc. are given elsewhere herein.

The fish to which the probiotic bacteria are administered to obtain a growth increasing effect are typically healthy fish.

Medical Uses of the Probiotic Bacteria

The probiotic bacteria of the present document may also be used for treating and/or preventing microbial infections in fish. Microbial infections include e.g. viral, fungal and bacterial infections, in particular bacterial infections. For example, the probiotic bacteria may prevent and/or treat infection caused by bacteria causing wounds, ulcers and/or lesions on the fish, such as on the skin of the fish. Other examples of infections that may be treated and/or prevented are infections causing septicemia. Bacterial infections causing wounds, ulcers and lesions in the skin of the fish may also cause septicemia when the bacteria enter the fish via the skin. Examples of bacteria which have been associated with such wounds/ulcers/lesions and/or septicemia are *M. viscose*, *Bizionia piscinecroseptica*, *Aliivibrio friggiae*, *Tenacibaculum maritimum*, and *Aliivibrio wodanis*.

Although the present document generally refers to "wounds" and the treatment/prevention of "wounds", the term wound (wounds) also encompasses ulcer(s), lesion(s) and the like which may equally well be treated and/or prevented by administration of the probiotic bacteria as disclosed herein. Wounds on the skin of fish may be caused e.g. by bacterial infection as further disclosed elsewhere herein. Also, wounds may be caused by injuries to the fish, for examples injuries caused by the close contact between individuals in cages, tanks etc. which may cause e.g. the fins of one fish harming nearby fish.

The creation of wounds/ulcers/lesions on the skin of the fish is also expected to present a route for entry for other pathogenic organisms. Acute bacterial infections in farmed fish that causes outbreaks with high loss in the population in a limited time creates a high concentration of bacterial pathogens that causes effective spread of the infection between the individuals in the population. Some of the fish pathogens causing epidemic outbreaks and infections of which may be treated and/or prevented by the priobiotic bacteria of the present document are *Aliivibrio salmonicida*, *Aeromonas salmonicida*, *Vibrio anguillarum*, *Edwardsiella piscicida*, and *Aeromonas hydrophila*. The ports of infection for bacterial pathogens are not well studied but both the gills, the intestine and the skin are considered important.

The present document is thus also directed to *Aliivibrio njordis*, *Aliivibrio balderis* and/or *Aliivibrio nannie* for medical use. The bacterial species may be used alone or in different combinations of two or more species and/or strains of a species.

The present document is further directed to a bacterium of the species *Aliivibrio njordis*, *Aliivibrio balderis* and/or *Aliivibrio nannie* for use in the treatment and/or prevention of a microbial infection in fish. The bacterial species may be used alone or in different combinations of two or more species and/or strains of a species.

Also, the present document is directed to the use of *Aliivibrio njordis, Aliivibrio balderis* and/or *Aliivibrio nannie* for the manufacture of a medicament for the treatment and/or prevention of a microbial infection in fish. The bacterial species may be used alone or in different combinations of two or more species and/or strains of a species.

Further, the present document discloses a method for treating and/or preventing a microbial infection in fish, said method comprising the steps of a) adding one or more species of probiotic bacteria to water, wherein the species of probiotic bacteria comprises or consists of *Aliivibrio njordis, Aliivibrio balderis* and/or *Aliivibrio nannie*; and b) exposing the fish to the water containing the one or more species of probiotic bacteria.

Bacterial infections which may be treated and/or prevented by the use of the probiotic bacteria disclosed herein include, but are not limited to, winter ulcer, friggiosis, wodanosis, bizioniosis, rainbow trout fry syndrome, bacterial cold water disease, cold-water vibriosis, and flexibacteriosis.

The probiotic bacteria of the present document may therefore be administered to the skin of the fish, i.e. topically, or via the gills to treat and/or prevent the infection by other microorganisms. Such application may be effected by bathing the fish in water containing the probiotic bacteria as disclosed elsewhere herein. Without wishing to be bound by theory, the probiotic bacteria of the present document may treat and/or prevent infections by occupying niches on the skin, thus preventing pathogenic bacteria from infecting the fish. Without wishing to be bound by theory, it is expected that the main treating/preventing effect on the microbial infection is contributed by the topical administration of the probiotic bacteria to the skin of the fish. The bacteria then traverse effectively the skin of the fish and ends into the subcutaneous tissues and the blood vessels of the body transporting the bacteria throughout the fish body.

Further details regarding the conditions during exposure of the fish to the probiotic bacteria, microbial infections etc. are given elsewhere herein.

The invention will be further described in the following examples, which do not limit the scope of the invention described in the claims.

EXPERIMENTAL SECTION

In the experimental section the three bacterial strains *Aliivibrio njordis* (B1-25, 18-1/2013 mandib VI1), *Aliivibrio balderis* (B1-24, 18-1/2013 kidn VI2) and *Aliivibrio nannie* (B8-24, 31-3/2013 kidn VI3) were used.

The bacterial cells were cultivated at a temperature of between 8 and 16° C. in Luria broth with 2.5% NaCl if nothing else is stated. The building of cultures took approximately 14 days and the cultures were semi-continuous since fresh sterile broth was added when the cultures reached the end of the exponential growth. The growth was relatively slow due to the lack of shaking and other motion of the cultures.

For the bathing, 2.55% natural marine salt was used during the bathing in Examples 1, 3 and 4, while full seawater (3.4%) was used in Example 2.

Example 1

Time period:
1 Oct. 2014-27 Jan. 2015 (117 days)
Tjeldbergodden settefisk AS (Njord Salmon AS), Aure, Norway
Stembiont (Probiotic) Bath Used:

Three different bacterial species of genus the *Aliivibrio* were used in a mix with equal amounts of each bacterial species. The novel bacterial species were 1. *Aliivibrio njordis* (B1-25, 18-1/2013 mandib VI1), 2. *Aliivibrio balderis* (B1-24, 18-1/2013 kidn VI2) and 3. *Aliivibrio nannie* (B8-24, 31-3/2013 kidn VI3).

The cultures of the three bacterial species were made in one liter flasks up to the point directly before a 9 hour transport from Oslo to Tjeldbergodden. Just before the transport (temperature kept between 8 and 15° C. during transport) all flasks were mixed in on plastic container with a volume of 25 liter, i.e. 24 liter in the 25 liter container. Just before the culture flasks were mixed they were fed with sterile fresh broth so the culture could be growing all the way to the site of application.

Atlantic salmon smolts in tank A4 were bathed for 1 hour in a 1/208 concentration of the equal mix ($5 \times 10^8$ cfu/ml in the 24 liter of mixed stock culture were mixed with 5 m$^3$ of 2.55% brackish salt water) of the three beneficial bacteria simultaneously at day 0. This gives a total calculated concentration of all three bacteria of $2.4 \times 10^6$ cfu/ml (i.e. total concentration of bacteria) and a cultivated concentration of $1 \times 10^7$ cfu/ml direct from the bathing water as estimated after growth on blood agar. Group A3 was control fish and not treated.

Post Smolts:

Atlantic salmon post smolt from Marine Harvest vaccinated intraperitoneally with a commercial vaccine 8 weeks (450 day degrees Celsius) before transfer to sea water at the freshwater smolt production facility were used. The smolts had an average weight of 80 grams when transferred to sea from the smolt plant on 1 Oct. 2014.

N=9800 fish (Salmo salar) in two groups, A3 (control) and A4 (treated) (4900 each) in 150 m$^3$ indoor tanks were used. The fish were kept in tanks during the entire 117 day study period.

A subset of 42 post smolts from A4 and 37 post smolts from A3 was weighed after transport to the aquarium research facility after 110 days.

The average weight of the 42 post smolts from A4 was 550.5 grams while the 37 post smolts from tank A3 had an average weight of 376.0 grams. This gives the 42 smolts sampled after 110 days from A4 an average weight gain of 46.4% more than the 37 post smolts sampled at the same time from the A3 control tank that was not bathed in a bacterial culture.

A subset of 150 fish in each group were weighed, measured and scored for ulcers after 117 days (A3) and 116 (A4) days (see FIG. 1).

TABLE 1

| Parameter: | Controls | Treatment group |
| --- | --- | --- |
| # of points: | 150 | 150 |
| Baseline weight (grams) | About 80 g | About 80 g |
| Mean weight (grams) | 530.97 | 699.79 |
| Weight gain (grams) | — | 168.82 |
| % weight gain | | 31.80% |
| p-value | — | <0.0001 |
| # ulcers | 87 | 46 |
| Chi square (two-tail) | — | <0.0002 |

Mortality of the fish measured by daily sampling of dead post smolts up to day 117 of the trial period was lower in A4; 140 dead post smolts (2.86%) than in the control tank A3; 188 dead post smolts (3.83%).

Results

The chosen concentrations of bacteria produced significant and measurable effect on weight gain and number of ulcers. Bathing time of 1 hour seems sufficient to achieve these effects with this concentration of bacteria.

The difference in weight and number of ulcers can be observed after 117 days given tank specific condition.

The sampling method was the same both at 110 days and one week/6 days later and given that the same representative post smolts were catched the control gained close to the same amount of weight during one week after 110 days. The explanation could be on available feed for the two tanks since the software at the facility estimating the amount of feed may have underestimated the growth in A4. The post smolts in both tanks gained more than 20 gram weight per day this week but limited feed could have restricted the growth in particular in A4 where the post smolts had had up to 46% better growth than in A3 in the period from approximately 60 days to 110 days of the trial.

Example 2

Time Period:
 15 Mar. 2015-2 Jul. 2015 (105 days)
 Tjeldbergodden settefisk AS, Aure, Norway
Stembiont (Probiotic) Bath:
 Three different bacterial species of genus *Aliivibrio* were used in a mix with equal amounts of each bacterial species. The novel bacterial species were 1. *Aliivibrio njordis* (B1-25, 18-1/2013 mandib VI1), 2. *Aliivibrio balderis* (B1-24, 18-1/2013 kidn VI2) and 3. *Aliivibrio nannie* (B8-24, 31-3/2013 kidn VI3).

The cultures were mixed in a large 1000 liter liquid container making the total volume to 600 liter including freshly added broth just before the shipping in a truck for 9 hours (temperature kept between 8 and 15° C. during transport). Before pooling in the large 1 m³ container tank the various three cultures had been incubated in 25 liter plastic containers that were first standing when the volume was small and then laid on the side when the volume increased. In this way the surface of the cultures should more easily take up air. The idea of the culturing is not to shake or having a high level of air into the culture, rather to have a more microaerophilic condition in a standing culture without shaking, only turning of the plastic cans 3 times during the day.

Fish in the two treatment tanks (E2 and E3) were bathed for 1 hour in an approximately 1/666 (E3) and 1/1333 (E2) dilution of beneficial bacteria at day 0 which is 1/3 and 1/6 of the culture dilutions used in Study 1. Fish in the third tank (E1) was control fish and not treated.

Post Smolts:
 Atlantic salmon post smolt from Belsvik smolt production plant (owned by Leroy Midt) vaccinated intraperitoneally with a commercial vaccine 8 weeks (450 day degrees Celsius) before transfer to sea water at the freshwater smolt production facility were used.

Figure 2:
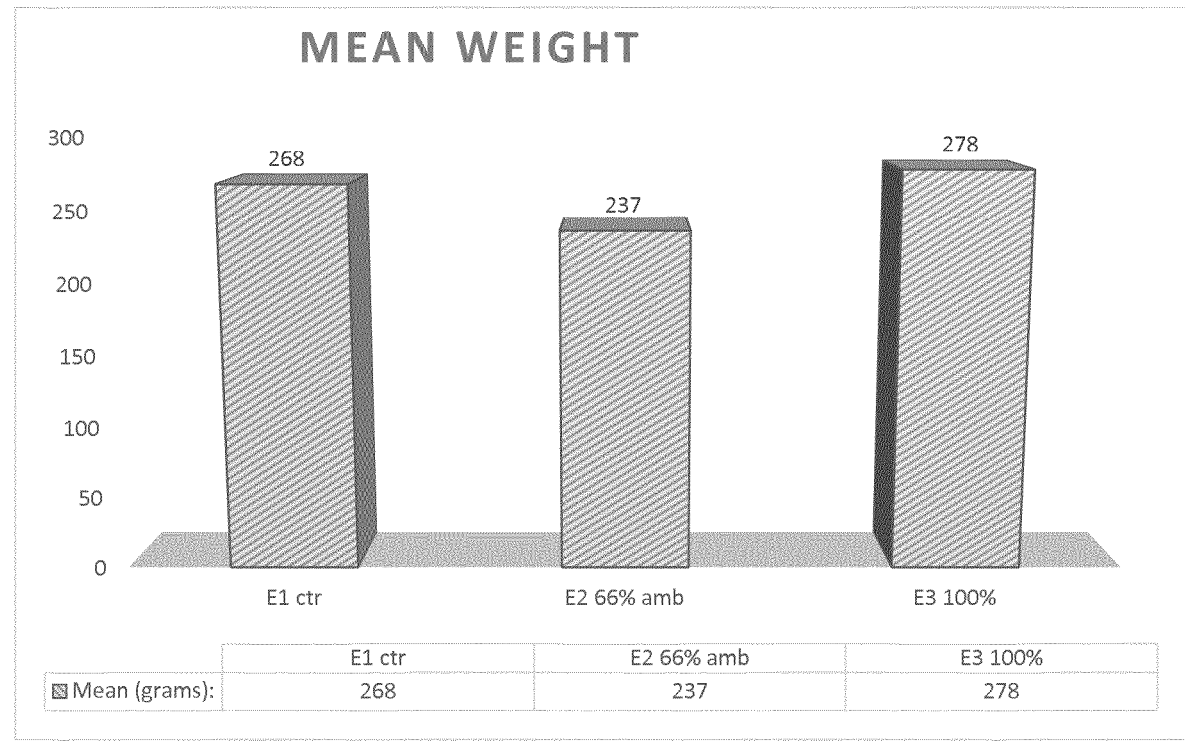
FIG. 2: mean weight of smolts bathed in equal amounts of *Aliivibrio njordis* (B1-25, 18-1/2013 mandib VI1), *Aliivibrio balderis* (B1-24, 18-1/2013 kidn VI2) and *Aliivibrio nannie* (B8-24, 31-3/2013 kidn VI3) according to Example 2.

N=99.622 fish (Salmo salar) in E1, N=109.300 in E2, N=98.754 in E3, i. e. the density of post smolts is 10% higher in E2 compared to E1 and E3. Fish were kept in the same tanks during the entire 105 day study period. A subset of 100 fish in each group were weighed, measured and scored for ulcers at day 73 and day 105 (see FIG. 2).

TABLE 2

| Parameter: | Controls E1 | Group E2 (17%) | Group E3 (33%) |
|---|---|---|---|
| # of points: | 100 | 100 | 100 |
| Baseline weight (grams) | About 80 g | About 80 g | About 80 g |
| Mean weight (grams) | 268 | 237 | 278 |
| Weight gain vs ctr (grams) | — | −31 | +10 |
| % weight gain | | −12% | +4% |
| p-value | — | worse | 0.08 |
| # ulcers | 52% | 46% | 36% |
| Mortality | 4.8% | 3.2% | 6.6% |
| Chi square (two-tail) | — | <0.0002 | |

Results

While reduced concentration of bacteria in the bacterial bath reduces efficacy of the treatment, at 33% of the concentration used in Example 1 a gain in weight (not statistically significant) and a reduction of ulcers (statistically significant) could still be observed as compared to untreated fish.

Example 3

Time Period:
 Spring 2016 (126 days)
 Tjeldbergodden, Njord Salmon, Norway
Stembiont (Probiotic) Bath:
 Three different species of *Aliivibrio* sp. (Tank A2: *Aliivibrio nannie*, Tank A3: *Aliivibrio njordis, Aliivibrio balderis* and *Aliivibrio nannie* 33% v/v and Tank A4: *Aliivibrio njordis, Aliivibrio balderis,* 50% v/v) were used in the same concentrations as in Example 1.

The cultures were grown in separate 25 liter plastic cans until shipping (temperature kept between 8 and 15° C. during transport) when the cultures for each A2, A3 and A4 tanks were mixed in one 25 liter container and fresh broth.

Fish were bathed for 1 hour in a 1/210 dilution of the cultures of beneficial bacteria which gives a bathing concentration of $1\times10^7$ cfu/ml at day 0. Fish in the third tank (A1) was control fish and not treated.

Post Smolts:
 Atlantic salmon post smolt from Belsvik smolt production plant (owned by Leroy Midt) vaccinated intraperitoneally with a commercial vaccine 8 weeks (450 day degrees Celsius) before transfer to sea water at the freshwater smolt production facility were used.

Figure 3:
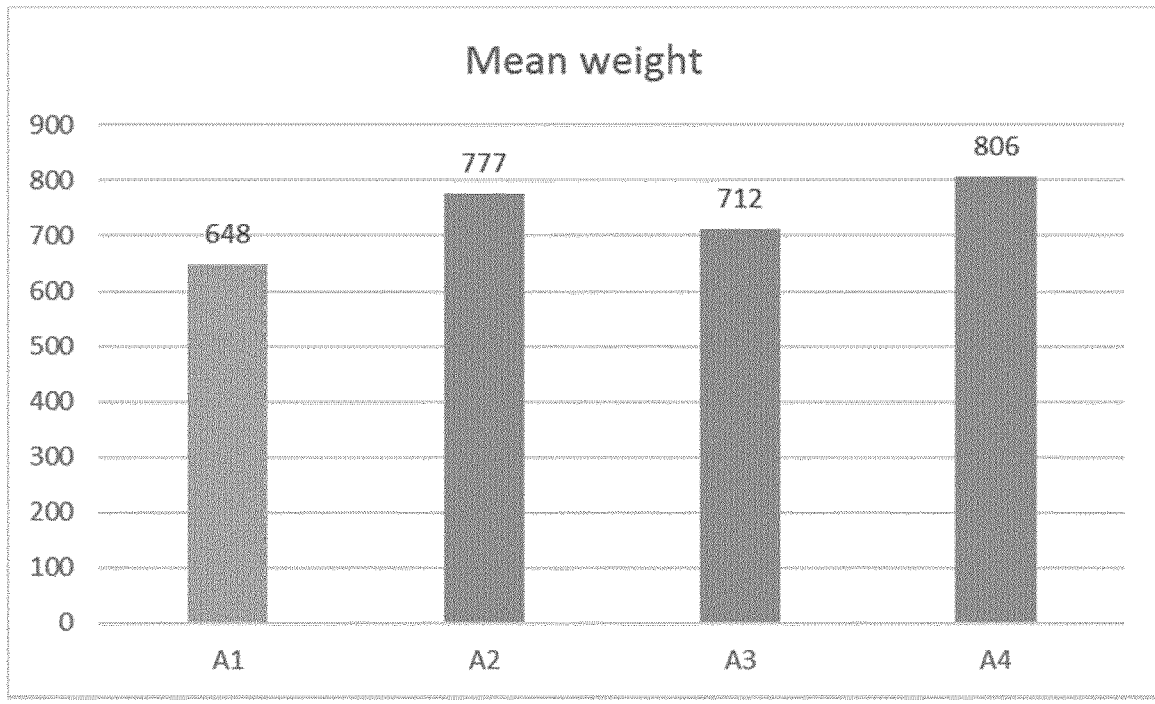
FIG. 3: mean weight of smolts bathed in different combinations of *Aliivibrio njordis* (B1-25, 18-1/2013 mandib VI1), *Aliivibrio balderis* (B1-24, 18-1/2013 kidn VI2) and *Aliivibrio* 20 *nannie* (B8-24, 31-3/2013 kidn VI3) according to Example 3.
Figure 4:
FIG. 4: Accumulated death of fish in Example 4.
Figure 5:
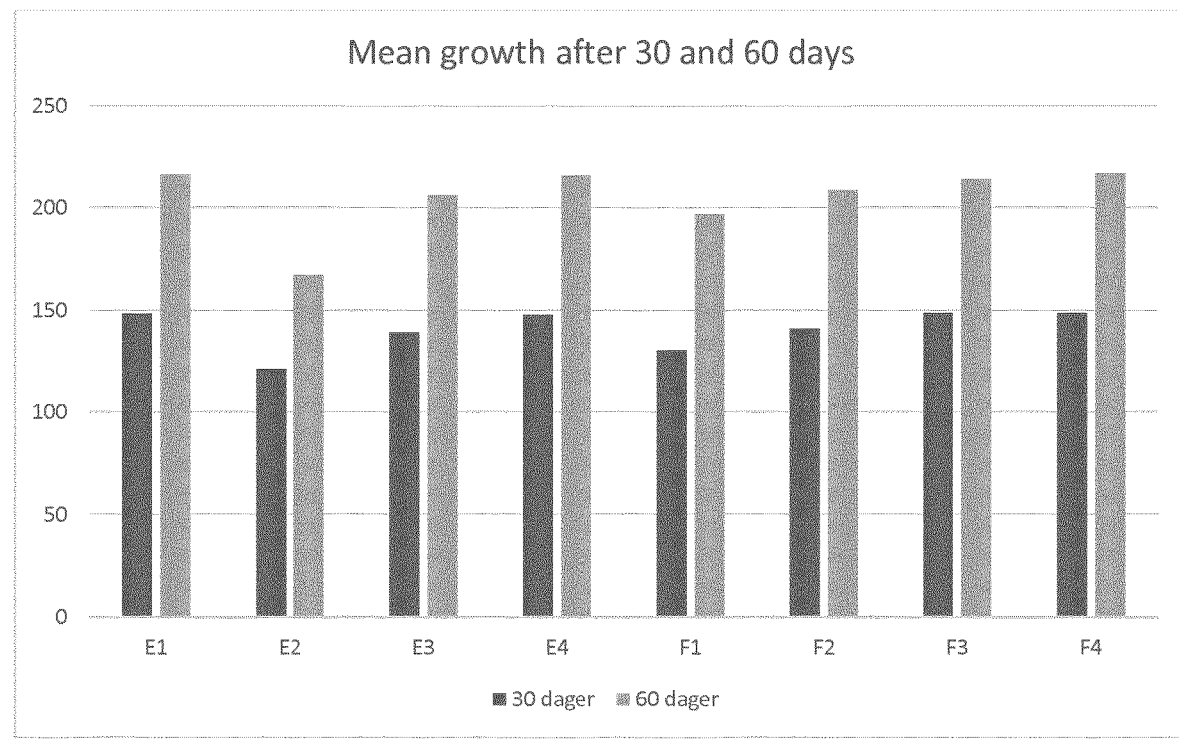
FIG. 5: Mean growth of fish in Example 4.
Figure 6:
FIG. 6: Mortality of fish in Example 4.
Figure 7:
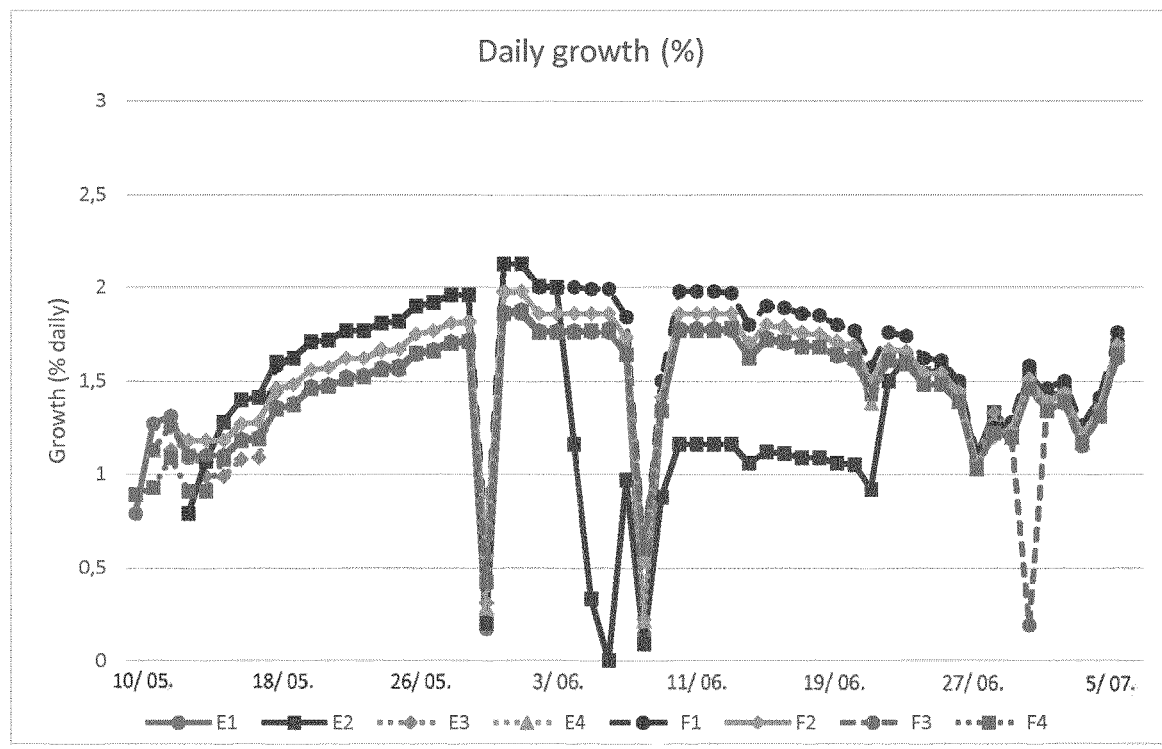
FIG. 7: Daily growth of fish in Example 4.
Figure 8:
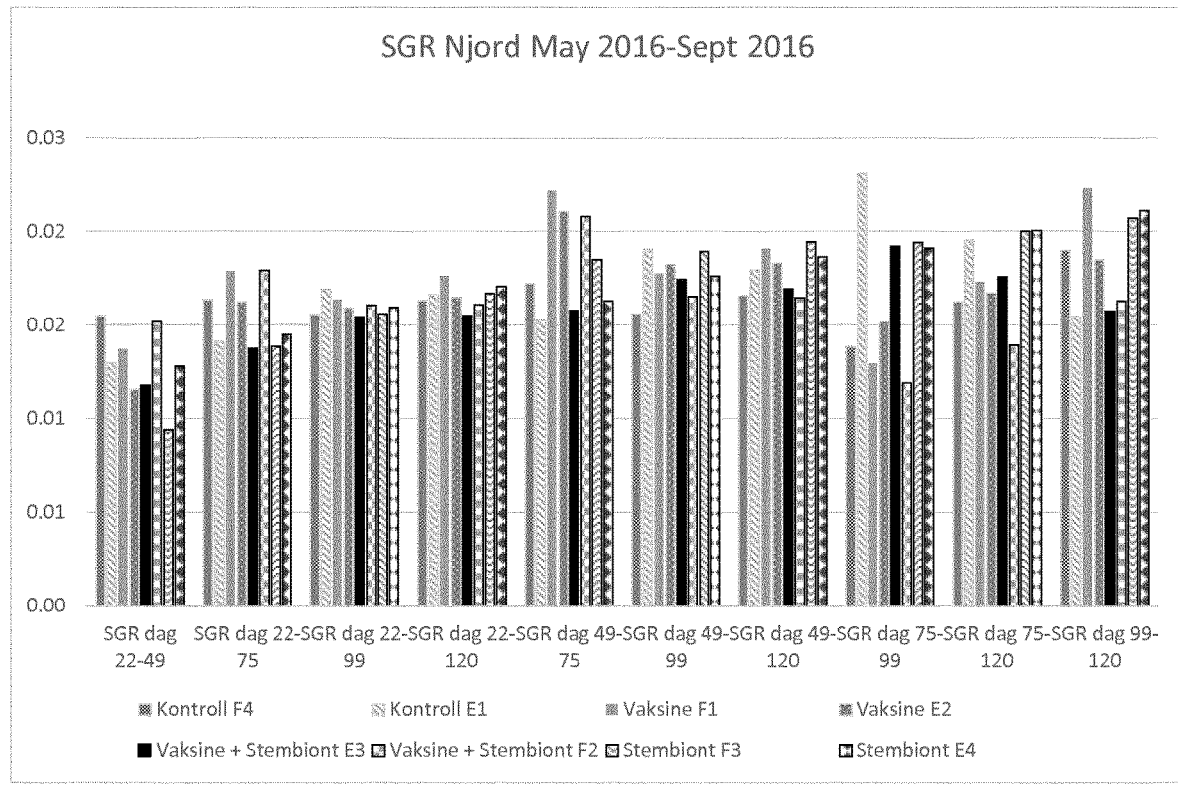
FIG. 8: Specific growth rate (SGR) in the various tanks and at the varying sampling time points in Example 4.

Fish were kept in tanks during the entire 126 day study period. At start it was 4000 fish in each of the 4 tanks. A subset of fish in each group were weighed, measured and scored for ulcers at day 72 and 126 during the study. Results in table from end of study (Day 126) (see also FIG. 3).

TABLE 3

| Parameter: | Controls A1 | Group A2 | Group A3 | Group A4 |
|---|---|---|---|---|
| # of fish subset: | 60 | 61 | 62 | 59 |
| Baseline weight (grams) | about 80 g | about 80 g | about 80 g | about 80 g |
| Mean weight (grams) | 648 | 777 | 712 | 806 |
| Weight gain vs ctr (grams) | — | 129 | 64 | 158 |
| % weight gain vs controls | | 20% | 10% | 24% |
| p-value vs controls | — | <0.0001 | 0.0097 | <0.0001 |
| Dead fish of total 3820 | 174 | 112 | 178 | 110 |
| Mortality | 4.55% | 2.93% | 4.66% | 2.88% |

TABLE 3-continued

| Parameter: | Controls A1 | Group A2 | Group A3 | Group A4 |
|---|---|---|---|---|
| Chi$^2$ (two-tail vs controls) | — | 0.0002 | 0.83 | <0.0002 |

Results

All tested combinations of strains showed a significant weight gain benefit over controls. *Aliivibrio nannie* used alone or *Aliivibrio njordis* and *Aliivibrio balderis* used in combination (1:1) showed a significant survival benefit over controls and when all three strains were used in combination (1:1:1).

Example 4

In this study 2×100 000 smolts were bathed in *A. njordis* and *A. balderis* in an equal mix (96.7%) and *A. nannie* (3.3%) for 1 hour in smaller indoor tanks and transferred to E4 and F3 on 10 May 2016, and 2×100 000 smolts were bathed in *A. njordis* and *A. balderis* in an equal mix (96.7%) and *A. nannie* (3.3%) for 1 hour in smaller indoor tanks and transferred to E3 and F2 after bath vaccination in the same tanks during the last 15 minutes.

To obtain the necessary 720 liters of cultures the cultures were grown in 39×25 liter plastic cans up to transport (temperature kept between 8 and 15° C. during transport) and added fresh broth just before shipping. The cans were not mixed but transported with 20 liters in each on the floor of the transport truck. The cans were opened once for letting in air during the transport on 1036 meter above sea level at the temperature of 12° C. for 30 minutes. The cultures were planned for two days of use with a time lag.

Bacterial cultivation from all volumes used in the small (150 m$^3$) indoor tanks used for bathing demonstrated a growth of the combination of *A. njordis* and *A. balderis* (96.7%) and *A. nannie* (3.3%) varying from 6×10$^5$ to 1.0× 10$^6$ cfu/ml bathing water.

At day 0, (19. May), day 22 (10. June), day 49 (7. July), day 75 (2. August), day 99 (26. August) and day 120 (16. September) after treatment and transfer to seawater, 80 post smolts were sampled, euthanized with anesthetic bath before weighing, measuring of length and autopsy (10 individuals from each tank). There were a small level of fin rot in all tanks at day 22 reduced to mostly fin rot in the back fin at day 49. At day 22 the cause of the fin rot were two other vibrio bacteria *Vibrio splendidus/V. tasmaniensis*) than included in the vaccines (commercial intraperitoneal vaccine at day minus 65 in the smolt plant and bath autovaccination in four of the eight tanks at day 0 against *Affivibrio wodanis* ans *Affivibrio friggiae*).

Two tanks were control tanks, two tanks were given probiotic alone, two tanks were given probiotic bacteria plus autovaccination (adding killed bacteria the last 15 minutes of the full hour as an autovaccine) in bath simultaneously and finally two tanks given only autovaccination.

After the three first samplings the last at day 49 it is evident that the control post smolts are performing well on the growth but starts to get bleedings and small ulcers on the ventral part of the body. The autovaccinated groups are growing almost as good as the control tanks. The probiotic treated tanks are showing less growth, statistically significant compared to the control tanks. However, the feed intake is as high as the post smolts in the control tanks. This indicates that the probiotic bacteria inside the post smolts demands energy to the post smolt to a larger degree than for the control post smolts and the autovaccinated post smolts.

The samplings at day 75, day 99 and day 120 continue to show that the unexposed control tanks were growing good and are having the largest weights, however not significantly larger than the other groups. Towards the end of the post smolt period before the post smolts were transferred by well boat to open sea cages the bathed groups were performing better than earlier in the trial but are not passing the control groups in average weight.

The expected daily growth in % i. e. specific growth rate (SGR) estimated from the 6 samplings in the trial shows that the two probiotic treated post smolt tanks have an even and relatively high SGR in the four last samplings compared to the control tanks and the bath vaccinated tanks. The SGR in the bath vaccinated tanks is calculated to be particular high during an outbreak of ulcer disease between day 49 and 75 and opposite relatively low during a second period with ulcers around day 75 to 99 in the trial. From the autopsy and cultivations this variation in the bath vaccinated groups indicate that *A. wodanis* is important in the first ulcer outbreak while the *Vibrio splendidus/tasmaniensis* is more dominant during the second ulcer outbreak.

See FIGS. 4 to 8.

Results a. The control post smolts (E1 and F4) have more small ulcers and bleedings in the skin than all the treated 6 tanks at the second and third sampling times.

b. The probiotic bathed tanks (E4 and F3) have the lowest weight but the highest feed consumption in the early part of the trial but towards the end of the trial the weight starts to increase relative to the other groups. This indicates that the post smolts are using extra energy to handle the good bacteria transferred through the skin on day 0 (May 10.). This indicates that the bacteria actually were transferred to the fish. The feed conversion rate is high for the probiotic treated fish and combined with more ulcer and bleedings in the control at some parts of the trial fits with similar data from the previous trials at Tjeldbergodden.

The specific growth rate (SGR) is stable high in the probiotic bathed post smolts from before 50 days into the trial and to the end of the trial on day 120. The SGR in the other groups in the trial including the control groups varies typically related to the type of bacterial pathogens causing infection challenge in the flow-through tanks with post smolts.

Example 5

In a post smolt facility with intake of marine water at 50 meter depth and with a flow-through system with UV disinfection of the intake water. This facility is the same as in Example 2 and 4.

In this study 2×100.000 smolts (tank E4 and F1) were bathed in *A. njordis* and *A. balderis* in an equal mix (96.7%) for 1 hour in a concentration of 1:600 while the tank volume was reduced to half, the inlet water stopped and oxygen were provided. These two probiotic bathed tanks were added bath vaccine for the 20 last minutes of the one hour bathing period with probiotic bacteria. In addition two tanks with 100.000 smolts in each (E1 and F3) were bath vaccinated with the same vaccine as used in the combined exposure with the probiotic exposure. The bath vaccine was applied in addition to the commercial ip vaccine that was given to all the smolt at the Belsvika smolt plant. The bath vaccine was the same as used in Example 4 and contained antigens against *Aliivibrio wodanis* and *Affivibrio friggiae* that has been isolated in post smolts with ulcer in the plant the previous season. *A. wodanis* has been the dominating pathogen in post smolt with ulcers in this post smolt facility for some years.

The probiotic cultures needed for this trial and for the trial in Example 6 was prepared for the last three days in a 750 liter fermentor as one single batch of 500 liter for each trial. These cultures were prepared with air blown into the culture medium. The cultures were drained into a food grade 1000 liter tank container and transported with a small truck in the first half of November when the outdoor temperature was between 5 and 10° C. on the route used.

At day 0, (2. Nov. 2016), day 15 (17. November), and day 128 (10. March) after exposure and transfer to seawater, 80 post smolts from each tank were sampled, euthanized with anesthetic bath before weighing, measuring of length and autopsy (10 individuals from each tank).

Four tanks were control tanks (E2, E3, F2 and F4).

Results

After 10 days from sea transfer an outbreak of fin rot and mortality caused by *Tenacibaculum dicentrarchi* occurred in the tanks, tank F1 (probiotic and bath vaccine) was loosing most post smolts but the outbreak was ending within one week after it started and the post smolt recovered fast. The fish had good appetite and growth rate in all tanks until the end of the trial when an outbreak of ulcer and mortality started the last week before the post smolt were planned to be transferred to open net pens in the sea. The outbreak was caused by the trout variant of *Moritella viscosa* that is not included in the commercial ip vaccine which probably explains why the outbreak occurred. All the tanks were treated with antibiotic in the feed and transferred to sea after an additional week. After being transferred to sea there was some increased mortality in particular in the vaccinated groups. This may be caused by the vaccineation against *A. wodanis* that produces a bacteriocin that inhibits *M. viscosa* and other bacteria at physiological salt levels within the body of the fish. Vaccination against *A. wodanis* makes it necessary to control by vaccine or other means the pathogens that are inhibited by the bacteriocin produced by *A. wodanis*.

Figure 9:
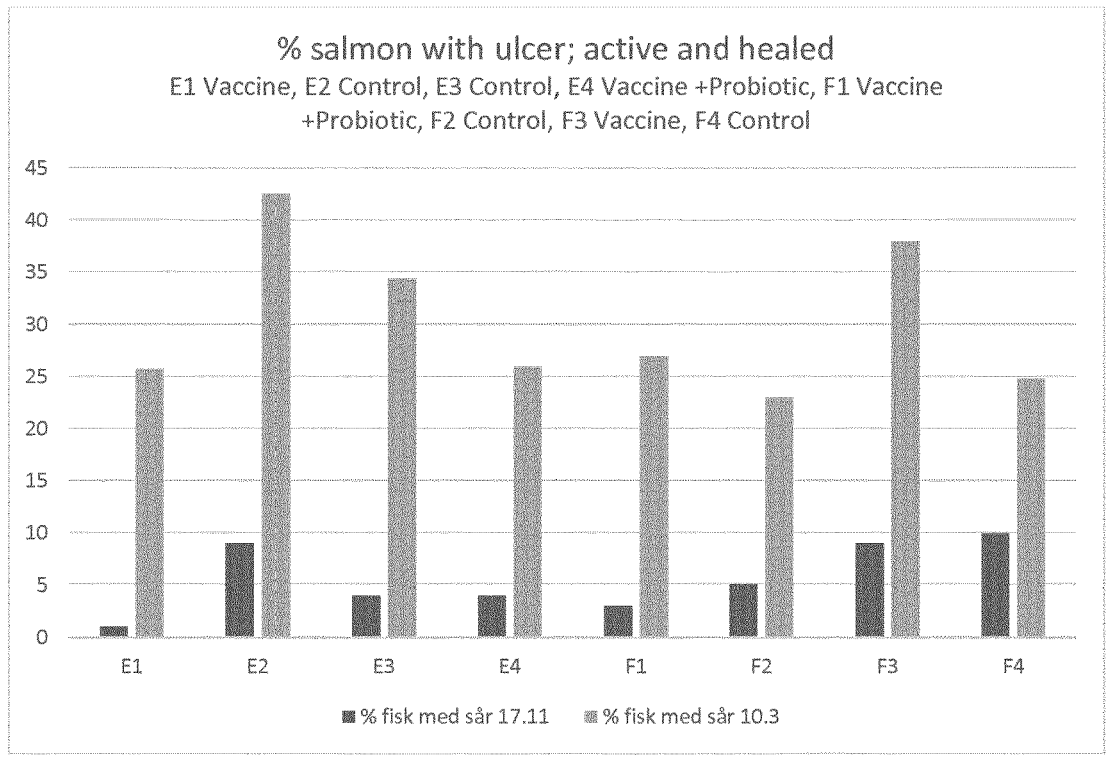
FIG. 9: Distribution of ulcers; active and healed in Example 4.
Figure 10:
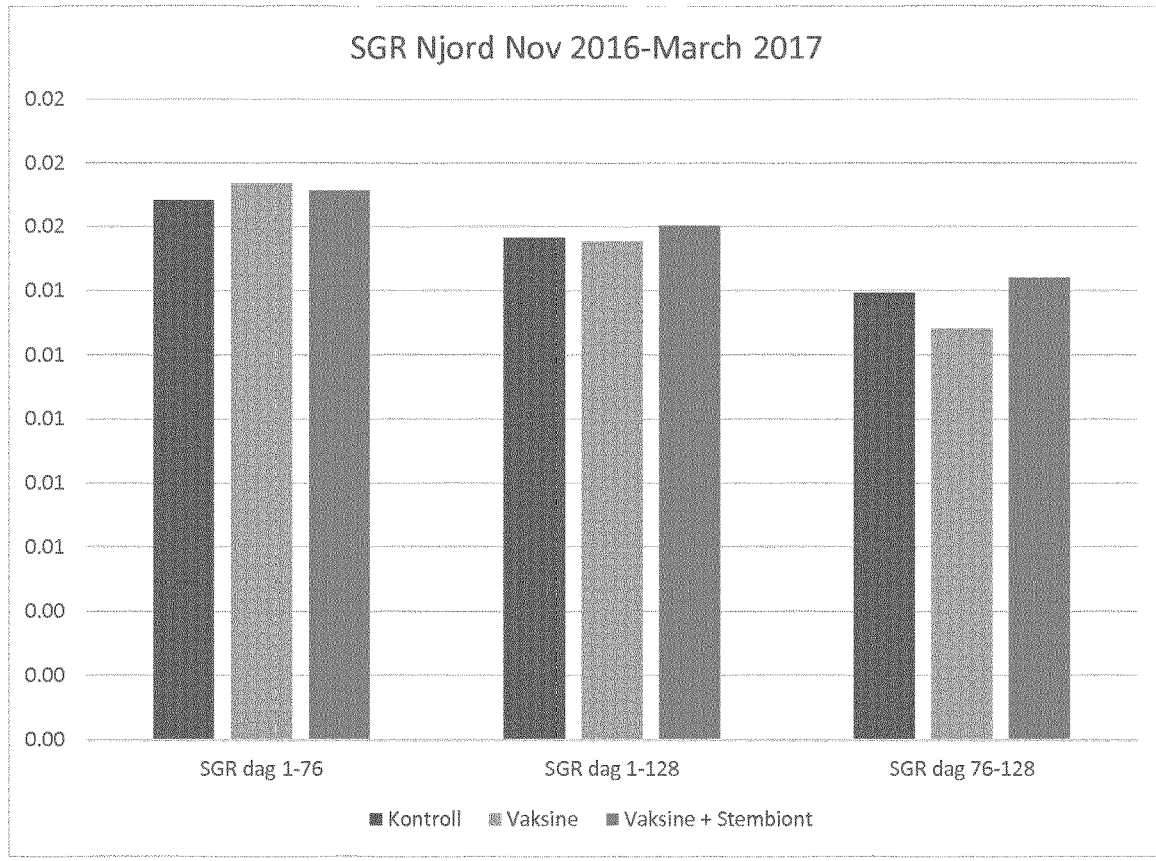
FIG. 10: Specific growth rate (SGR) in the compiled trial groups in Example 5.

The probiotic exposed tanks had fewer post smolts with ulcer than the control tanks and the vaccine tanks. On the last sampling (17. March-17) the tanks with probiotic exposure had 5% less ulcers than the other tanks (see FIGS. 9 and 10).

Example 6

Exposure to Probiotic Marine Bacteria at Sea Launch after Bath Vaccination Against *Aliivibrio wodanis* Four Weeks Earlier This industrial trial was performed with vaccination and probiotic treatment in the smolt plant before the smolts were kept 5 months in 4 closed sea cages of 3000 m³ to avoid sea lice exposure. The seawater was pumped from 26 meter depth and used undesinfected.

Design Summary and Exposure

Salmon fry were vaccinated with a commercial intraperitoneal vaccine 8 weeks before sea launch. In addition they were bath vaccinated in freshwater tanks in the smolt plant when they were having the size of approximately 40 gram, 4 weeks before sea launch. When the smolts were above 80 grams and had developed the additional immunity from the bath vaccination where they immersed in probiotic bacteria in the concentration of 1:600 with an equal mixture of the bacterial species *Aliivibrio njordis* and *Aliivibrio balderis* for one hour before they were transported a short distance in a well boat to the closed net pens. Each of the four tanks contained 100 000 smolts and the combined probiotic exposed and bath vaccinated smolts were kept in two tanks (M1 and M2) while the control tanks were not bath vaccinated nor exposed to probiotic bacteria.

Results

The bath vaccinated groups had a significant higher growth rate the four weeks before sea launch. Theoretically this can be speculated to be caused by exposure to brackish water that contain the ulcer pathogen *Aliivibrio wodanis* 6 days before sea transfer.

After bathing the immersion vaccinated groups in probiotic bacteria the growth rate was higher in the exposed groups up to the last part of the trial. The last 2 months of the trial resulted in some low mortality of between 1 to 2 percent starting in control pen M3. A couple of weeks later ulcer and slightly increased mortality occurred in the three other closed pens. In the last month of the trial control group M3 recovered very well from ulcers and the growth rate became very high. M3 used to have the largest smolts from the start of the trial before the growth rate was the lowest during the major first part of the trial before it compensated the lost growth at the end of the trial. The other control group continued to have a lower growth rate compared to the bath vaccine and probiotic exposed groups.

Figure 11:
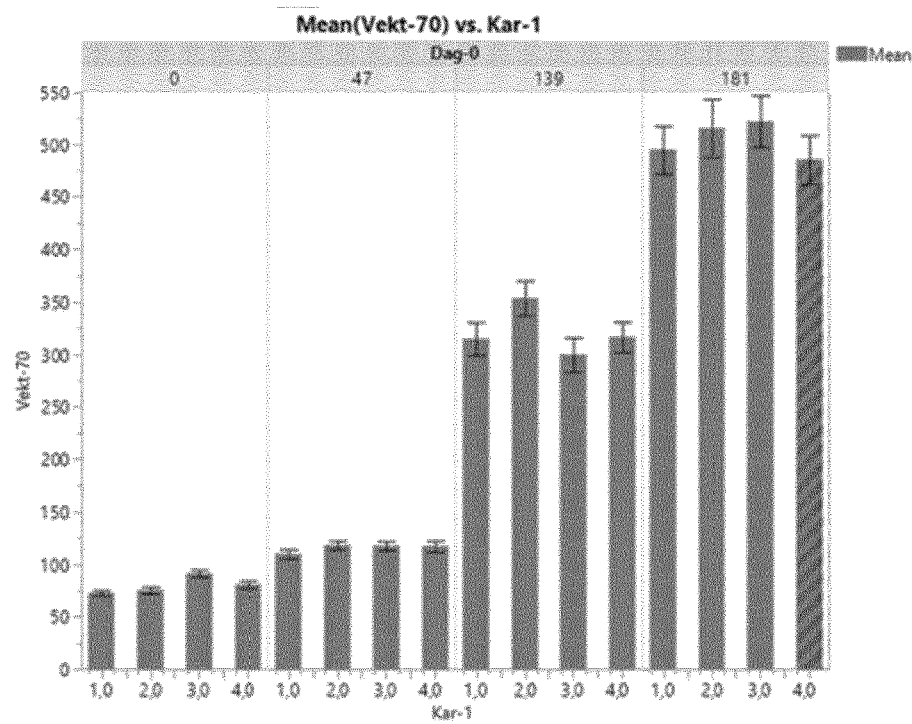
FIG. 11: The mean weight of the post smolts in the four closed pens at various sampling points in Example 6.
Figure 12:
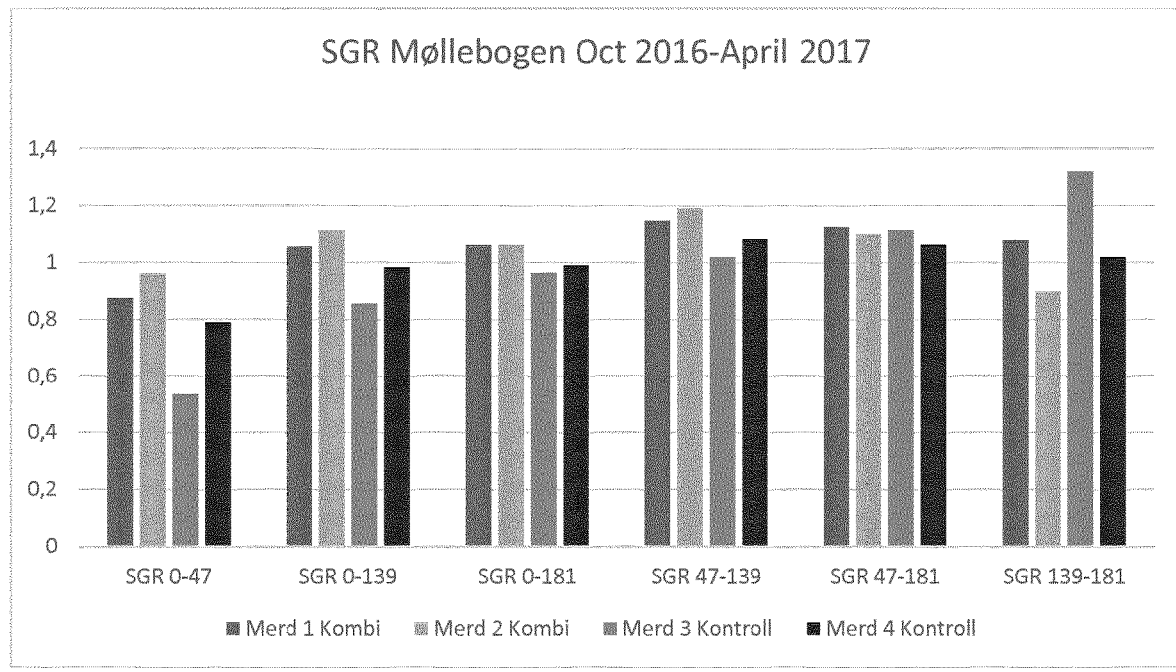
FIG. 12: Specific growth rate (SGR) in the various closed pens and at the varying sampling time points in Example 6.
Figure 13:
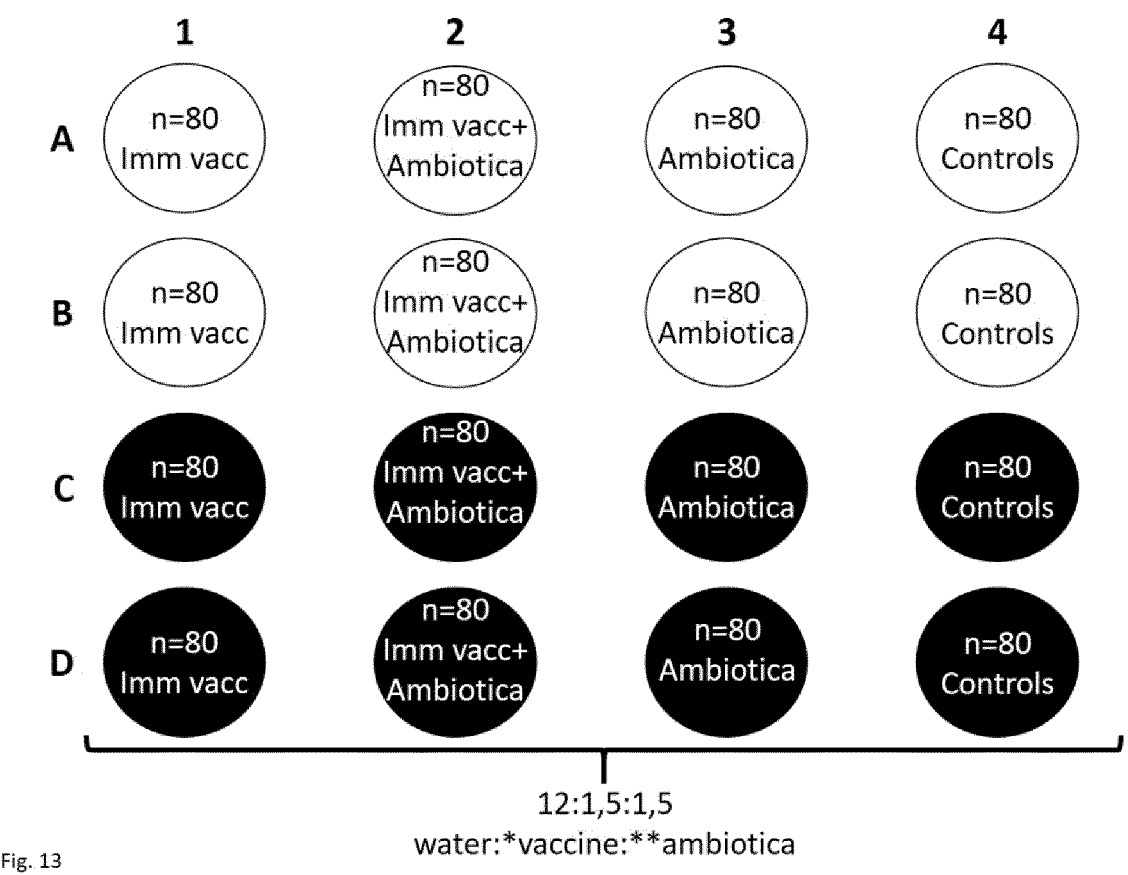
FIG. 13: Overview of the experimental design and tank set-up in Example 7. Example: fish in row 1 was the placebo group, fish in row 2 received a combined treatment with an immersion vaccine and beneficial bacteria, fish in row 3 received beneficial bacteria only and row 4 were controls. A and B (green) were duplicates and all have a 21-day immunization period before subjected to seawater. C and D (blue) were duplicates and were put on seawater immediately after exposure. All exposure were blinded according to blinding schedule below (table 3).
*Vaccine or placebo. **Probiotica or placebo.
Figure 14:
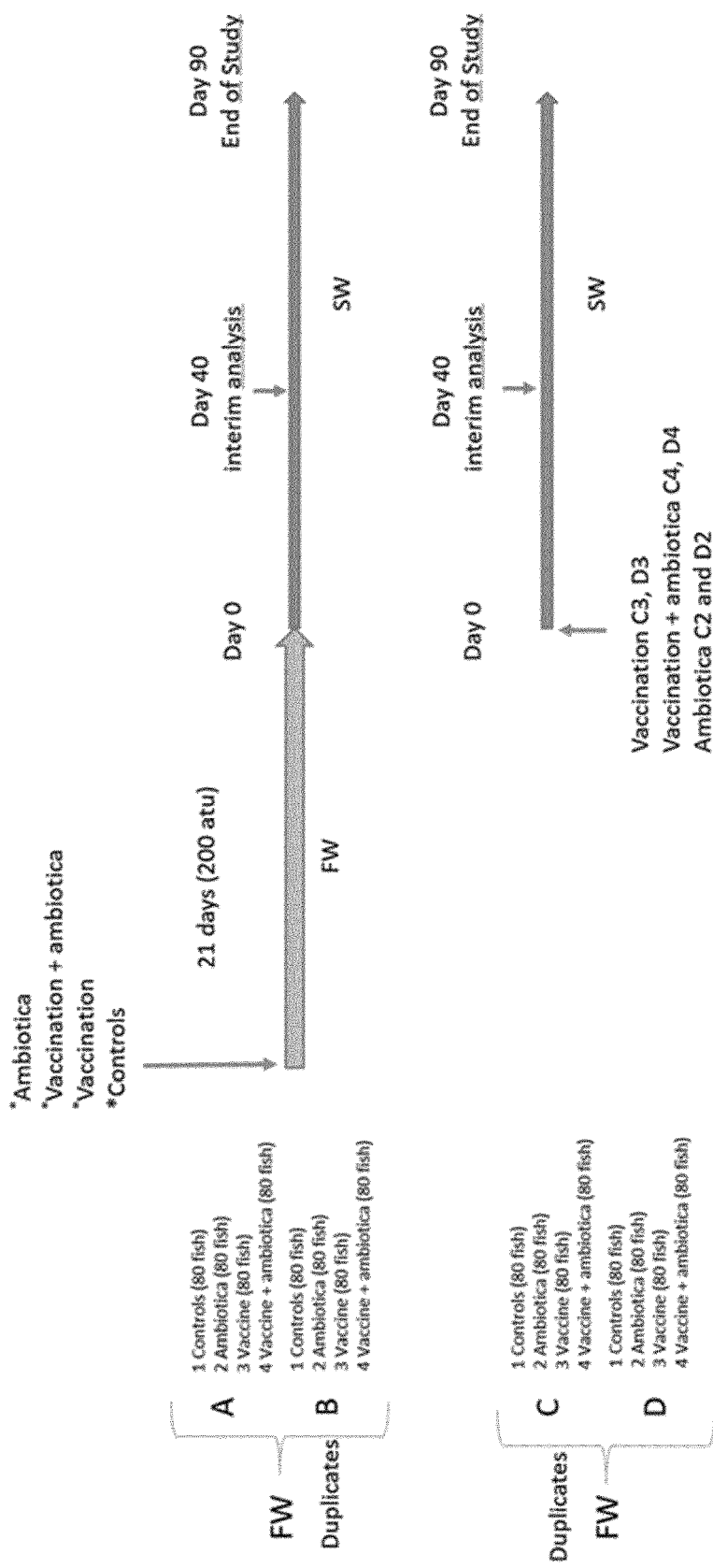
FIG. 14: Detailed sketch of the experimental protocol in Example 7.
Figure 15:
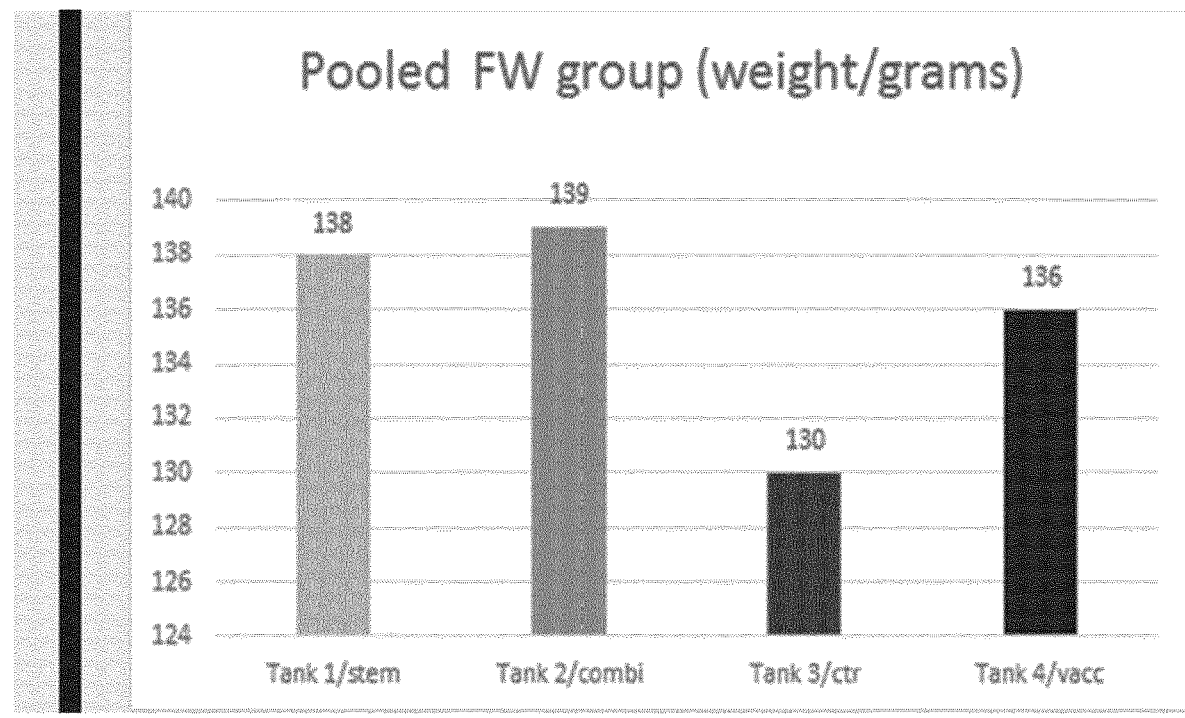
FIG. 15: Weights in average in the freshwater (FW) part of Example 7.
Figure 16:
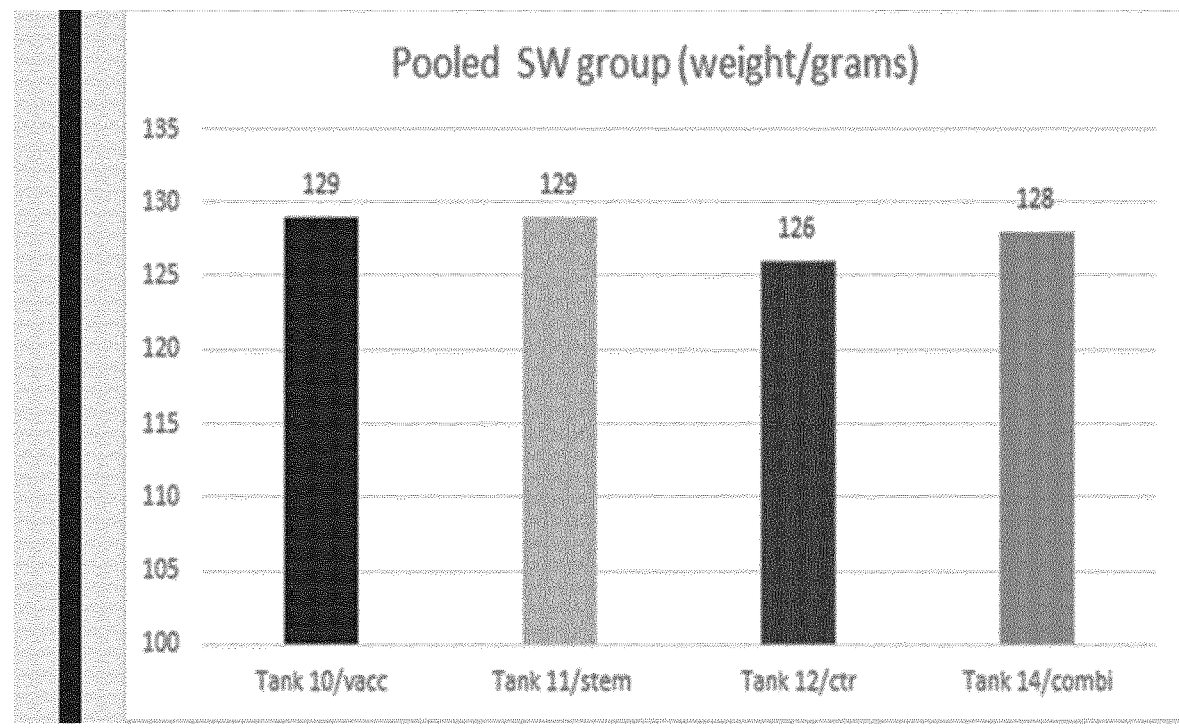
FIG. 16: Weights in average in the saltwater (SW) part of Example 7.
Figure 17:
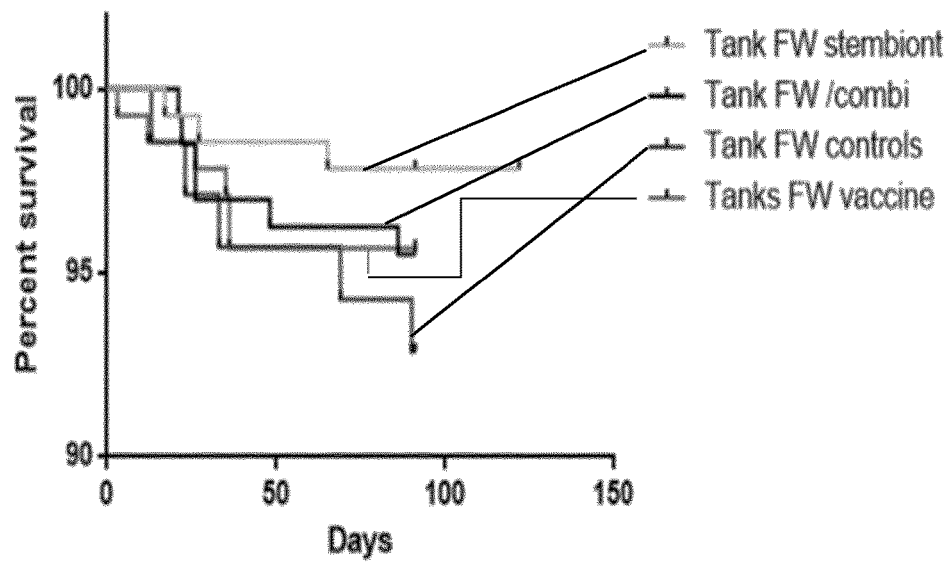
FIG. 17: Survival curves of the various groups of the freshwater (FW) part of Example 7.
Figure 18:
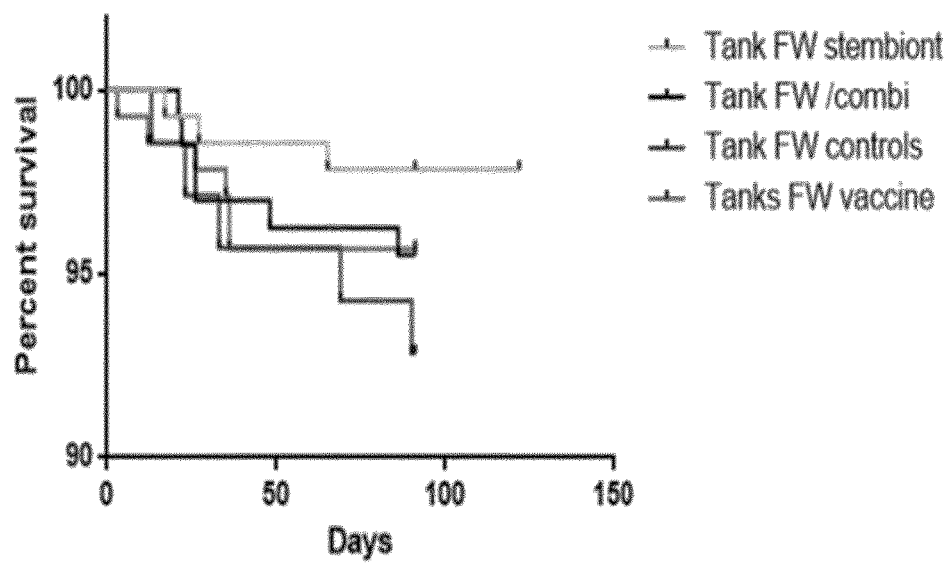
FIG. 18: Survival curves of the various groups of the freshwater (SW) part of Example 7.
Figure 19:
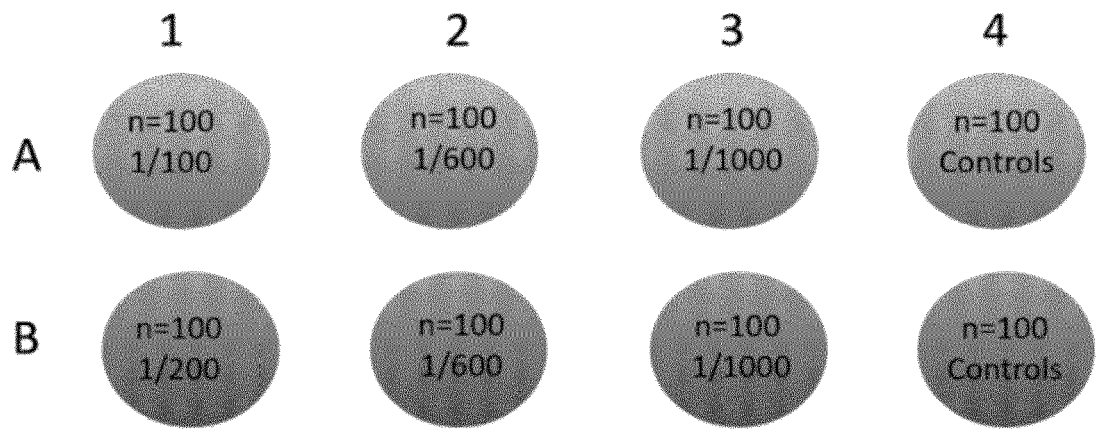
FIG. 19: Overview of the experimental design in Example 8.
Figure 20:
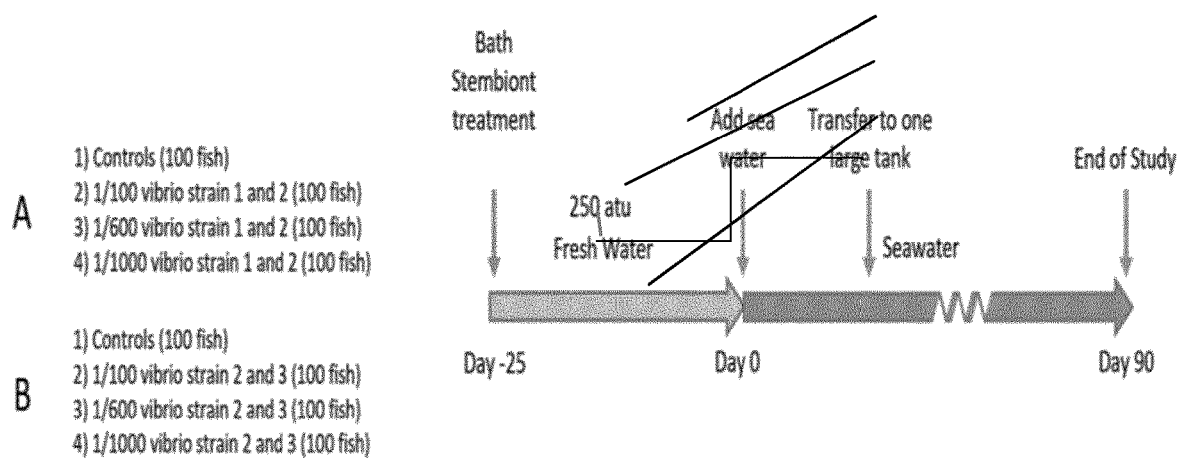
FIG. 20: Detailed sketch of the experimental protocol in Example 8.
Figure 21:
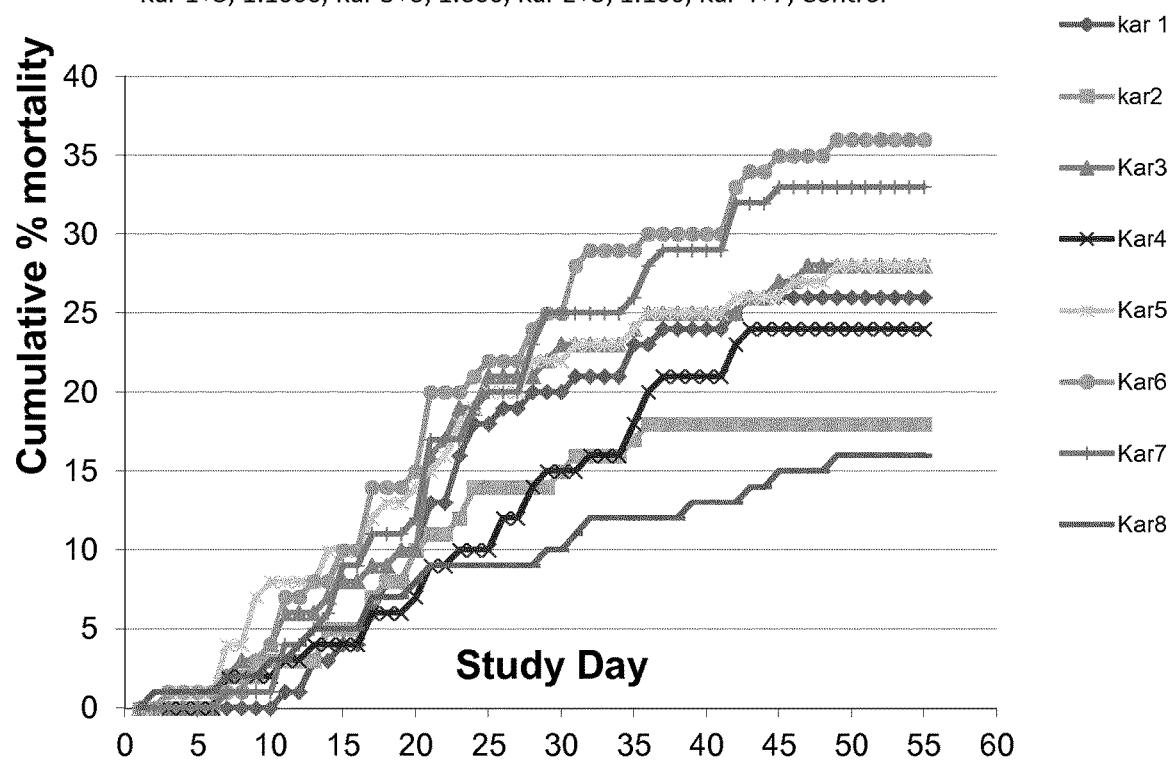
FIG. 21: Cumulative mortality curves of the various trial groups in Example 8.
Figure 22:
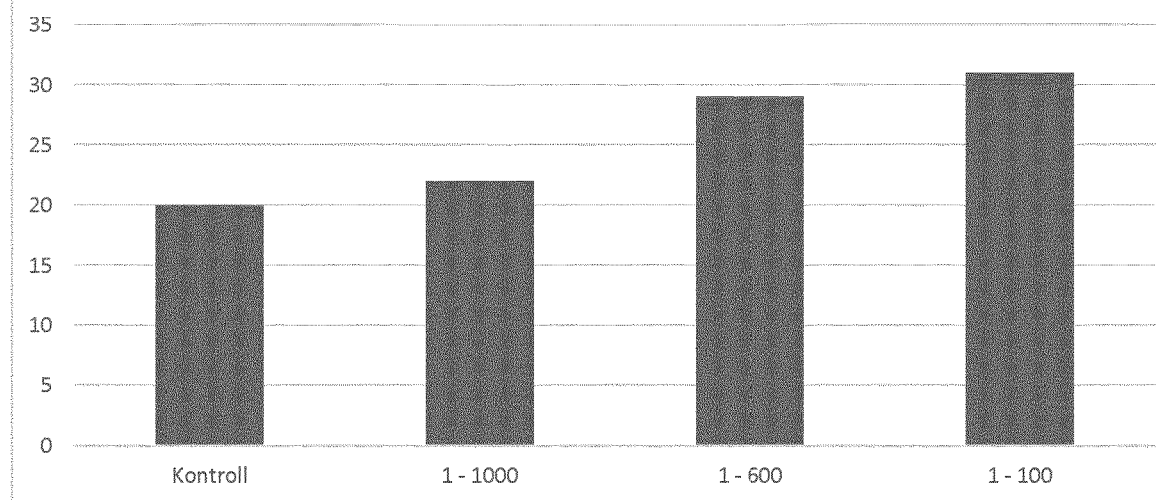
FIG. 22: Number of post smolts above 200 grams in the various trial groups in Example 8.

After transfer to open net pens in the sea the mortality in all four populations continued to increase to more than 4 percent being highest in the vaccinated and probiotic handeld post smolts. The reason for the increased mortality after transfer to sea pens could speculated to be caused by transport in a period with increasing infections. The cause of the increased mortality in the sea was *Alivibrio wodanis* against which the bath vaccine was prepared for protecting the post smolt from. It may also be the speculated that the duration of the vaccine was reduced after more than 7 months since bath vaccination. Normally the effect of a bath vaccine will be good for at least four months (see FIGS. 11 and 12).

Example 7

Onset Requirements and Efficacy of Treatment of Salmon by Use of Biotic Enhancement in Combination with Immersion Vaccine To determine if a period of onset for the immersion vaccine is needed for full treatment effect and whether an add-on effect of biotic treatment is present and if this differs between fish with an onset period and fish with no onset period. Safety and efficacy by survival, number of ulcers, weight gain and feed conversion ratio of Atlantic salmon bathed in a biotic preparation of a mixture of two live innocuous bacterial cultures of *Aliivibrio* spp. (*A. njordis* and *A. balderis*) in combination with an immersion vaccine will be compared between two treatments groups, and within subgroups receiving different treatments. Comparators were untreated controls and controls treated with immersion vaccine or biotic treatment as single agent. One group of fish was challenged by natural salt water immediately after treatment while a second group was given a period of 21 days in fresh water before exposure to sea water.

This study was a confirmation of the benefit of a 60 second static dip treatment with immersion vaccine, a combination of an immersion vaccine and biotic treatment or biotic treatment alone compared to untreated controls.

The immersion vaccine consisted of 11 different bacterial pathogens including the known pathogens causing epidemic infections like vibriosis, cold water vibriosis and furunculosis in addition to known and novel pathogenic bacteria causing ulcers and fin rot.

Objectives:
1. to investigate whether co-treatment with an immersion vaccine and a mix of probiotic bacteria is safe
2. to investigate whether a period of onset is needed to reach significantly better effect (mortality, morbidity and weight) of chosen treatment (see endpoints) compared to fish treated without an onset period
3. to investigate whether treatment with either an immersion vaccine, or a mix of beneficial bacteria or a combination of the two results in higher survival rates, and/or weight gain, and/or lower rates of any moribund signs, including darkening, lethargy, and presence of specific disease signs, such as ulcer formation, fin rot or mouth rot compared to untreated controls.

End Points:
End points for the first objective were survival (days), ulcer formation (scoring table 4) and weight (grams) during the first 21 days of treatment without exposure to sea water. End points for the second objective were survival, weight and ulcer formation (number and severity) during the period after sea water. End point for third objective was morbidity signs including but not restricted to ulcers, darkening of the skin, fin rot, anorexia and mouth rot. Ulcers were scored by size (largest diameter) and severity.

Test Product
Strains of bacteria to be used as augmenting were two non-pathogenic *Aliivibrio* spp. strains (*A. njordis* and *A. balderis*) produced in such a way that certain proprietary methods are used to manifest desirable culture characteristics.

The immersion vaccine contained a selection of inactivated bacteria produced in such a way that certain proprietary methods are used to manifest desirable culture characteristics.

TABLE 4

Description of experimental fish

| | |
|---|---|
| Species | Atlantic salmon (*Salmo salar*) |
| Strain | Mowi |
| Origin | Eggs from Tveitevåg, Presmolt from Fister Smolt AS |
| Average weight | Average = ca. 60 grams (weight range 50-70 g) |
| Physiological status | Smolts L:D = 24:0 |
| Number of fish | 80 fish in each of sixteen treatment groups to a total of 1280 fish |

Populations entered in to the study were documented to be free from exposure to the disease confirmed at source/before entering the study. It was anticipated that the fish will have a stock density of about 20 g/liter and at the end of the study the density will be ca. 40 g/liter.

Husbandry Management
The fish and tanks were tended and monitored on a daily basis by an aqua medicine biologist.

Dead fish were collected daily. Environmental parameters were recorded daily. Abnormal or moribund behaviour, loss of appetite, increase in appetite or unexpected increase in mortality were reported.

The fish were hand fed. The amount was adjusted by biomass calculations once a week, and adjusted by weighing after 40 days.

TABLE 5

Overview of management

| | |
|---|---|
| Temperature | 8 ± 1° C. |
| Water flow | Min. 0.8 l/kg/min |
| Water discharge | Tube overflow system |
| Cleaning | Once a day |
| Photoperiod regime | L:D = 24:0 before and during trial |
| Feeding | Hand fed 1% through the day, 5 days a week. |
| Oxygen | Normal 7.8 mg/l, min. 5 |
| Salinity | 34 ± 1 |

Main Inclusion Criteria and Post Exclusion Removal
Clinically healthy Atlantic salmon (*Salmo salar*) in good health status and known vaccination status. Mean size was approximately 50 g.

Mean weight of 100 fish at entry was recorded. Mortality in the tanks was recorded daily. Dead fish were assessed for presumed cause of death and categorized for the presumed cause. As defined by the investigators, discreet periods of explained and unrelated loss such as physical damage, oxygen depletion, starvation or any other unrelated incidence were censored. Dead fish were kept to determine what further investigation was necessary. Mortality was confirmed by necropsy, and either by pathology and/or a positive bacteriological result were considered specific loss.

The study was conducted at Solbergstrand in Frogn in Akershus county and run from approximately mid-June 2016 and for 110 days.

Design Summary
The study should last for 111 days (21 days+90 days) or until the biomass reached 50 kg pr. tank—whatever came first. Eighty fish in each of sixteen treatment groups to a total of 1280 fish were included. The set-up consisted of two main groups with two sub groups receiving either an immunization period of 21 days after being exposed in fresh water before put in seawater at day 21 (Group 1-A and B), or no immunization period but subjected to sea water immediately after exposure (Group 2-C and D). Each sub group A/B/C/D was divided in 4 groups whereof 3 received different treatment and a fourth was a control group (FIG. 1).

All fish received exposure when in fresh water. Group A and B stayed in fresh water for 21 days after exposure while group C and D were entered into SW immediately after exposure. Exposure of all groups took place for a short period in brackish water.

Tanks A and B, and Tanks C and D were duplicates in order to compensate for tank to tank variability.

Volume used: 500 ml probiotica/placebo and 500 ml vaccine/placebo and 4 liter of water per dip tank/bucket.

Five fish were dipped for 60 seconds each time. This was repeated 32 times so that all 160 fish from two tanks (e.g. A1 and B1) were treated in the same bath.

The study will last for approximately 111 days with an interim analysis after 40 days. Cumulative mortality rate is predicted to be 16% in the treatment groups and 40% in the control groups.

Day 0 and Day −21 Definition
Day 0 is the day which all fish is put on salt/sea water. For group A and B Day −21 is the start of treatment with the biotic and/or immersion bath. For group C and D treatment starts at Day 0.

All groups will be treated in SW, also groups treated with two probiotica, before fish are put back in rearing tanks with fresh water (A and B) or directly in salt/sea water (C and D).

Blinding and Marking

Fish in the treatment groups will be kept in separate tanks during the experiment. The study will be double blinded and fish will be randomly selected to each tank. Persons not involved in the daily treatment of fish or analysis of the data will perform blinding of the treatment. Two envelopes with the codes will be kept and not opened until end of data analysis.

TABLE 6

Added volumes of placebo/vaccine/ambiotica were 1500 ml each in 12 liters of water. The responsible person carrying out the exposure did not know what was in the flasks. The table is only an example of how the combination could look like.

| Treatment | Vaccine | Ambiotica | Random Tank |
|---|---|---|---|
| Placebo or vaccine and placebo or ambiotica | Aα | Bα | AB/CD |
| Placebo or vaccine and placebo or ambiotica (not same as α) | Aβ | Bβ | AB/CD |
| Placebo or vaccine and placebo or ambiotica (not same as α or β) | Aγ | Bγ | AB/CD |
| Placebo or vaccine and placebo or ambiotica (not same as α, β or γ) | Ao | Bo | AB/CD |

Example: Greek letters for exposure and capital letters for tank. Combination α (which may contain any of the treatment) was given to one random tank in group A, B, C and D.

The same went for the other treatments. The person blinding the study registered what treatment went in what tank and stored the code in a locket envelope. The blinder was involved in exposure during the study or the data handling after the study.

Probiotica/placebo were identified with corresponding numbers (Aα, Aβ, Aγ or Ao) whereof two were only containing medium without live bacteria. Flasks with vaccines were identified by a letter (Bα, Bβ, Bγ or Bo) whereof two were having placebo and two contained vaccine. All flasks were covered by tin foil. One tube vaccine went with one flask probiotica and blinded (table 3 above).

All fish were PIT tagged prior to study start.

Observations and Interim Analysis

During the observation period all mortalities were classified. The records of feeding were kept for each tank being studied. Concentration of beneficial bacteria were measured on fish at 4 time points for all groups by drawing blood from 5 fish. The first time was 5 minutes after first treatment for all groups receiving probiotic treatment before they were put into the tanks. The second time at Day 0 and the third time at the time of the interim analysis at Day 40. At least 5 fish were analysed at end of Day 90.

Weight

Fish were weighed and measured at start by average of 100 fish and every individual at the end of the study in all 16 tanks. At day 40 an interim analysis was performed where mean weight and survival were calculated for each tank based on diseased fish up to day 40.

Bacteriological Examination During and End of Study

Fish that died during the observation period and was classified as mortalities and diseased (MD), weight and length measured and kept refrigerated for bacteriological culture and examination. Quantification of bacterial load was performed on 5 fish from each of the 16 treatments tanks at day −21, day 0 day 40 and at all surviving fish at end of study. At end of study it was be drawn blood from all living fish and they were weighed, measured and bacteria cultivated.

Results

When the probiotic is applied in a 1:8 concentration as a 30 second dip in the freshwater 3 weeks before the smolt is launched into seawater there is an improved growth rate compared to the control group. The combination of dip in probiotic bacteria and dip vaccination is also increasing the growth rate compared to vaccination alone. The unexposed control group has smolts with the lowest growth rate among the trial groups. If the exposure to probiotic and dip vaccine is performed at the time of sea launch the differences in growth rate between the experimental groups have the same tendency but the differences are minimal which underlines that it is beneficial to dip salmon in probiotics and bath vaccine some weeks before sea launch (see FIGS. 13, 14, 15, 16, 17, and 18).

Example 8

Effects of Different Combinations of *A. njordis, A. Balderis* and *A. nannie* and Effects of Various Concentrations of the Probiotic Bacteria Study Objectives To determine what combination of three different strains of innocuous *Aliivibrio* sp. in combination 1 (*A. njordis*) and 2 (*A. balderis*), and 2 (*A. balderis*) and 3 (*A. nannie*), with a 30-minute static bath treatment immersion vaccine will result in the lowest mortality and largest weight gain versus untreated controls over a total of a 65-day period. All groups were given a period of 95 days (approx. 950 atu) in fresh water before exposure to sea water.

Sub-Objectives 1. to investigate if and what two strain combination and concentrations of probiotic bacteria will be most effective for weight gain compared to controls
2. to investigate what and if treatment with a mix of probiotic bacteria will result in higher survival rates, and/or weight gain, and/or lower rates of any moribund signs, including darkening, lethargy, and presence of specific disease signs, such as ulcer formation, fin rot or mouth rot compared to untreated controls.

Study End Points

End points for the objectives were survival, ulcer formation, weight, specific growth rate and feed conversion rate. Morbidity signs including but not restricted ulcers, darkening of the skin, fin rot, anorexia and mouth rot. Ulcers were scored by size and severity.

Test Product

Strains of bacteria used as augmenting are three non-pathogenic *Aliivibrio* sp. produced in such a way that certain proprietary methods are used to manifest desirable culture characteristics (Table 5 Listing of Substances) The strains will be a combination of strain 1 (*A. njordis*) and 2 (*A. balderis*) (treatment A), and strain 2 (*A. balderis*) and 3 (*A. nannie*) (treatment B).

Description of Experimental Fish

| | |
|---|---|
| Species | Atlantic salmon (*Salmo salar*) |
| Strain | Mowi |
| Origin | Eggs from Tveitevåg, Presmolt from Fister Smolt AS |
| Average weight | Average = ca. 50 grams (weight range 40-60 g) |

-continued

| Physiological status | Smolts L:D = 24:0 |
| --- | --- |
| Number of fish | 80 fish in each of ten treatment groups to a total of 640 fish |

Design Summary

The study lasted for 160 days (95 days+65 days). One hundred fish in each of 8 treatment groups to a total of 800 fish will be included. The set-up consisted of two main groups, A and B, receiving probiotic bacteria *Aliivibrio* spp. in brackish water in different concentrations, and an immunization period of 95 days (950 au) after treatment in fresh water. Around day 80 (when biomass reached maximum density which is about 40 g/liter) all fish were put together in a large tank with seawater for the remainder of the study (FIG. 1). Fish in the control group were treated with placebo (solution with no bacterins/bacteria).

Volumes of Stembiont™ for each dilution is described in table 3. Cumulative mortality rate was predicted to be 10% in the treatment groups and 20% in the control groups. Dead fish from any causes will not be replaced in the separate groups after study.

Day 0 was the day which all fish received salt/sea water. For group A and B Day −95 is the start of treatment with the biotic bath.

Fish in the treatment groups were PIT-tagged and kept in separate tanks during the experiment. The study was double blinded and fish were randomly selected to each tank. Persons not involved in the daily treatment of fish or analysis of the data performed blinding of the treatment. Two envelopes with the codes were kept and not opened until end of data analysis. All fish were weighed at the time they were PIT-tagged. When fish were treated the fresh water in the 200 liter tanks, with 180 liter water, was lowered to 90 liters. The tanks were immediately filled with salt water back to approximately 180 liters (see table 3 for exact volumes) to obtain ca 17 ppt salt concentration which is the preferred Stembiont™ salt concentration. Then the Stembiont™ was added. The fish stayed in the water treatment for 30 minutes before the brackish water was replaced with new fresh water. Salinity was measured during the 30 minutes' treatment and the water was oxygenated.

All fish were weighed and measured at start and at end of study. When the biomass reached ca 40 g/liter which was approximately day 40, all fish were transferred to one large tank.

Fish that died during the observation period were classified as mortalities and diseased (MD), weight and length measured and kept refrigerated for bacteriological culture and examination. At end of study all fish were weighed, measured and bacteria cultivated.

Mortality, mean weight, weight gain, size, relative percent survival, survival curves and number of ulcers on surviving fish were calculated and compared between all groups. All variables were calculated from start to transfer to the large tank, from start to end of study and from transfer to large holding tank to end of study.

Results

The average weight at the end of the trial was 169 (−3/+5) grams in the eight groups. Only 6 days after switching from freshwater to 2.5% salt water an outbreak caused by *Moritella viscosa* started in the common tank and the mortality increased increased for two weeks before it was going down gradually. After three weeks of mortality both *M. viscosa* and *Aliivibrio wodanis* was isolated from ulcers and the head kidney for the next 3 to 4 weeks. This disease outbreak was a classical winter ulcer outbreak occurring naturally even if the intake water was UV-desinfected. The mortality varied from 20 to more than 35% between the 8 groups in the same tank. Both the groups with probiotic diluted 1:100 had mortality close to 20% while one control group had 34% mortality, the other control group had 26% mortality. There was seen both a dose effect on the mortality and a probiotic strain combination effect on the mortality.

The numbers of salmon with weight higher than the average in the group was higher in the group immersed 30 minutes in the strain combination 1 and 2 compared to the combination of the strains 2 and 3 which is in agreement with the results for the growth rate in Example 3. This tendency to a larger number of fish with weight higher than the average weight in the group compared to the two control groups is similar in all the three dilutions of probiotic bacteria used for the bathing (see FIGS. 18, 19, 20, and 21).

Example 9

Testing Various Physical and Biological Parameters that Interacts with the Uptake of Probiotic Bacteria in the Blood of Atlantic Salmon Atlantic salmon (Salmo salar) 30-60 grams non-smoltified parr and 80-100 grams smolts, in total 426 fish.

Inclusion/Exclusion Criteria

Inclusion criteria morphology: Only healthy, intact and sexually immature fish without apparent visual deformities or behavioural abnormalities was used in the trial.

Husbandry Management Prior to Study Start

The fish were acclimatized according to local protocol requirements (NIVA). The fish and tanks were tended and monitored on a daily basis. Dead fish was collected daily and environmental parameters were recorded daily. Abnormal or unexpected behaviour, loss of appetite or any unexpected increase in mortality were reported immediately.

TABLE 7

Overview of management

| Salinity | Freshwater |
| --- | --- |
| Stocking density | Max 20 kg/m$^3$ - at day 0 |
| Temperature | 12° C. ± 1° C. |
| Water discharge | Tube overflow system |
| Cleaning | Once a day |
| Photoperiod regime | L:D = 24:0 before and throughout trial period |
| Feeding | By hand |

The protocol is designed to comply with European Pharmacopoeia monographs:

Design Summary

Atlantic salmon smolt (or fry) are kept in freshwater. Bacteria was diluted in seawater where salt water bacteria was used. Smolt or fry left for a certain time in bacteria (se set up below). Fish were normalized in a seawater mixture before being put back to freshwater where Stembiont™ are dying in freshwater. Blood sampling after 5 min in freshwater. Benzokain used as anaesthesia for blood sampling. Salmon euthanized by overdose.

For Tests A to D 165 Fish was Used.

Culturing from the blood 3 smolts and 6 parr as negative controls gave growth of an average of 36 cfu/ml blood of with 9 of the 18 controls with 0, 10 or 20 cfu/ml (i. e. 0, 1 or 2 colonies per plate).

A. Time of bathing; use log 7 (dilution 1:10 will be used, approx. log 7) as the total concentration and *A. njordis*, *A.*

*balderis* and *A. nannie* as the bacterial combination (Test 2). Six fish at each time point were used. 3 controls are included for baseline.

| | |
|---|---|
| 60 min | 8836 cfu/ml blood |
| 45 min | 9020 cfu/ml blood |
| 30 min | 9723 cfu/ml blood |
| 15 min | 4123 cfu/ml blood |
| 10 min | 4283 cfu/ml blood |
| 5 min | 893 cfu/ml blood |
| 3 min | 2858 cfu/ml blood |
| 1 min | 4383 cfu/ml blood |
| 30 sec | 607 cfu/ml blood |

The results indicate that the minimal length of bathing salmon in probiotic bacteria to gain maximal concentration of probiotic bacteria in blood is approximately 30 minutes. Half of that concentration is achieved after 10 to 15 minutes. At shorter time intervals of 30 seconds to 5 minutes the uptake of bacteria seem to vary more but uptake about one third of the uptake occurring after 30 minutes is occurring B. Concentration of Stembiont™; 5 min was used and 1, 2, and 3 combination (Test 3). Six fish at each time point were used.

| | |
|---|---|
| log 4 | 130 cfu/ml blood |
| log 5 | 122 cfu/ml blood |
| log 6 | 1890 cfu/ml blood (615 cfu/ml blood from bath 2, 3166 cfu/ml blood from bath 1) |
| log 7 | 893 cfu/ml blood (from A) |
| (log 8) | (undiluted culture approx log 7) |

The results a clear dose dependence for the bathing water in uptake of probiotic bacteria in blood, the higher concentration the higher uptake rate.

C. Salt concentration in the bathing water; 10 min was used and 1, 2, and 3 combination (dilution of 1,2,3 combination from Test 1 in 1:10 in salt and fresh mixtures made first) (Test 4). Six fish at each time point were used.

| | Growth |
|---|---|
| 0 ppt | 3+ |
| 5 ppt | 4+ |
| 10 ppt | 3+ |
| 15 ppt | 4+ |
| 20 ppt | 5+ |
| 25 ppt | 4+ |
| 30 ppt | 4+ |

Grading of growth from blood after bathing of salmon in bacterial cultures of varying salinity: 5+ means regular number in most fish and high density, 4+ high density of bacteria in blood but varying density between various fish, 3+ lower density and varying number in various fish individuals The results indicate that a wide interval of salinity can be used in the immersion solution from freshwater to marine water but with some more optimal results when bathing the fish in 20 ppt compared to lower and higher salt concentrations.

D. Stembiont™ combination; 5 min was used and log 7 (non-diluted culture was used) as the total concentration (Test 1), Six fish at each time point were used. Strain 1 is *Aliivibrio njordis*, Strain 2 is *Aliivibrio balderis* and strain 3 is *Aliivibrio nannie*.

| Probio strain | Cfu/ml blood |
|---|---|
| 1, 2, 3 | 3000 and 2500 |
| 1, 2 | 3000 and 2000 |
| 3 | 400 and 1500 |
| 1, 3 | 60 and 1000 |
| 2, 3 | 200 and 2500 |
| 1 | 2500 and 200 |
| 2 | 3500 and 1000 |

The results of the strain combinations on the concentration of bacteria in blood indicates that use of all three strains or strain 1 and 2 gives the highest and most regular concentrations of probiotic bacteria in the blood of salmon. Strain 1 seems to dominate in the mixed culture above strain 2 and 3. Strain 2 seems to dominate in the mixed culture with strain 3.

For test E, F, G and H 3 smolts or fry per parameter 29×3=87 will be used. Blood sampling with vacutainer and plating on 2 blood plates with 2.5% NaCl from each blood sample i.e. 87 blood samples plates×2=174 blood plates, incubated at 10° C. for 3-7 days.

A full set of parameters for all three categories E, F and G 87×3=261 fish were used E. Different status of smolt related to seawater (Test 5)
I. Smolt directly from freshwater; result: Approx. 3000 cfu/ml blood but more irregular distribution.
II. Smolt from same batch but kept for 7 days in full seawater; result: Approx. 2000 cfu/ml blood
III. Post smolt kept in full seawater from July 2016; Approx. 1000 cfu/ml blood The results indicate that pre-smolt stage may be absorbing high numbes of probiotic bacteria but at a more uneven distribution. The ready smoltified salmon seems to absorb a high and even concentration of bacteria in blood. The smolt that has been 7 days in full seawater seems to be somewhat "saturated" with probiotic or similar bacteria but will still absorb about half of the bacteria that is absorbed at sea launch.

F. Different temperatures of the bathing water; use 5 min bath, non-diluted culture (log 7) of 1, 2 and 3, full sea-water (Test 6). Two types of salmon were used, one smolt of 120 gram staying in freshwater ready for seawater and one parr (35 g) staying in freshwater. Six of each type were used for each temperature a total of 12 fish and 12 plates seeded with 0.1 ml blood on the surface.

| | Smolt | Parr |
|---|---|---|
| 4° C. | 1430 | 3824 |
| 6° C. | 1620 | 1630 |
| 8° C. | 1318 | 6325 |
| 10° C. | 1993 | 413 |
| 12° C. | 782 | 1023 |
| 14° C. | 633 | 382 |
| 16° C. | 627 | 6923 |
| 18° C. | 913 | 417 |
| 20° C. | 1540 | 12600 |

The results indicate that large smoltified salmon is taking bacteria over the skin best at temperatures below 10° C., above 10° C. the number of bacteria taken up in the blood seems to reduced to half the number. The parr may take up higher concentrations of bacteria pr. ml blood possibly because of the smaller size of the fish body. However, the variation in uptake seems to be more large than with the smolt.

G. Old culture (VI1 og VI2 from Bindalssmolt produced at Glycanova, Øra, Fredrikstad, transported to Bindal 20-21/11-16, used 22/11-16 and returned 22/11-16 to Oslo via Tjeldbergodden and then stored in empty container outdoor with freezing etc. until 20/12-16 then diluted 1:2 in tank with sterile freshwater and tapped and stored at 6° C.) (Test 7)

Need 3×2 Fister salmon in salt water=6 Fister salmon
Need 6×2 blood agar plates with NaCl=12 blood agar plates w/NaCl
Results (6 Salmon, 2 Agar Plates from Each Fish)
  a. Glycanova (fermentor) 9 week culture, dilution 1:100: 182 cfu/ml blood
  b. Glycanova (fermentor) 9 week culture, dilution 1:600: 508 cfu/ml blood
  c. Glycanova, 1 week old culture (18° C.) of *A. njordis* and *A. balderis:* 55 cfu/ml blood
  d. Glycanova, fresh culture of *A. njordis* and *A. balderis:* 469 cfu/ml blood
  e. Lab culture, *A. njordis*, fresh culture: 77.5 cfu/ml
  f. Lab culture, *A. balderis*, fresh culture: 182 cfu/ml
  g. Lab culture, *A. njordis*, one week old: 57.5 cfu/ml
  h. Lab culture, *A. balderis*, one week old: 57.5 cfu/ml Cultures a and b are possibly contaminated with different bacteria growing in the old 9 week culture.

There is a clear increase in probiotic bacteria in blood when the culture is fresh compared to one week, somewhat more than the double amount in the blood when culture is fresh compared to one week old.

H. Various bacterial cultures; use 5 min bath, non-diluted culture (log 7) Bacteriological examination from blood samples was performed on 100% of the fish.

No other samples was taken.

Blood samples (0.1 ml) from each fish is plated on two agar plates. The mean number of CFUs will be the unit used for calculation of differences in uptake of bacteria between treated fish.

Results

The various factors to be set to an optimized use of the probiotic bacteria *A. njordis, A. balderis* and *A. nanniae* seems to be mapped. The robustness of the biological system related to these bacteria and the intimate contact with fish seems to be high. Good results from the probiotic use may be expected in a wide specter of many parameters tested in Example 9. Possibly one of the most important parameters is the concentration of the probiotic culture. I. e. the higher concentrations of bacteria the higher number of bacteria is taken up within typical minutes to half an hour as the optimal time period. However dilutions of cultures down to 1:1000 can produce measureable positive effects. Salinity, temperature strain combination do not have very strong impact making it necessary to be strict on these parameters in the protocols used.

Conclusions

The probiotic bacteria called *Aliivibrio njordis, Aliivibrio balderis* and *Aliivibrio nannie* are involved separately or in different combinations in the 9 studies (Examples 1 to 9) of this application. The application of these probiotic bacteria has so far been tested in research aquaria with group sizes of +/−100 fish and in intermediate sized industrial setups with typical 4.500 individuals in the groups and finally in industrial post smolt farming involving groups of typically 100.000 fish in each tank.

In the research aquaria important intervals for various parameters necessary for practical protocols for use of the three probiotic bacterial species in the fish farming industry has been established.

From Example 9 it is evident that the probiotic bacteria can be beneficial at all time interval tested for bath application from 30 seconds to one hour. Shorter exposures than 3 minutes seem to be enough to obtain one third of the transfer of the probiotic bacteria to the blood of the salmon compared to 30 minutes that seems to be the shortest and most optimal time period to obtain high uptake of the probiotic bacteria to the blood of Atlantic salmon.

The experiments with bathing salmon point clearly that there is an increasing uptake of probiotic bacteria to the blood of salmon when the concentration of the probiotic bacteria in the immersion water is higher. There seem to be beneficial to bath fish in all concentrations of the probiotic bacteria and dipping fish in dense concentrations of bacteria as 1:10 dilution has been shown to be efficient when the dipping is occurring for only 30 seconds. Designing good and practical bathing strategies based on varying the concentration of the probiotic bacteria and the time period of immersion makes the protocols that can be developed applicable to many different industrial operational procedures of fish farming.

Various salt concentrations of the immersion for bath or dip with the probiotic bacteria seem to be of no major impact since effective bathing can be made in various concentrations of salt from marine salt water to freshwater. It may seemingly be a small optimum to use 2% salt in the bathing solution compared to higher or lower salt concentrations.

Both from the aquarium experiments with bathing fish and from the industrial studies in the application it seems that the combination of *A. njordis* and *A. balderis* is more effective than including *A. nannie* in the probiotic exposures.

Atlantic salmon can be effectively bathed in all kind of life stages with good effect on growth and disease prevention. However, it seems that smolts ready for the see\awater bathed before or at sea transfer is more evenly absorbing the probiotic bacteria than earlier in the freshwater phase on the smolt plant. In addition it seems to be some reduced uptake of these probiotic bacteria after some days in seawater. It is potentially competition between bacteria in the sea to approach and connect to the microbiota of Atlantic salmon.

The temperature of the immersion with probiotic bacteria does not have a major impact on the uptake of bacteria to the blood. Temperatures between +4 and 20° C. have been tested and there may be a slightly higher uptake in the lower temperature range than from 10° C. and up to 20° C. However, these differences seem to be minor and maybe related to variations for fish to fish individual when the temperature is in the higher range.

The age of the probiotic culture does not seem to have a major impact for the uptake of probiotic bacteria within the range of one week when the culture is stored at +18° C. However, when the culture is made dense in an aerobic atmosphere like in a fermentor a reduced uptake may be of importance by storage. This difference is not seen so clearly when lab cultures with lower density are used From all the trials and examples.it seems that the probiotic protocols are solid but that the bathing concentrations of 1:600 is in the lower range to get results that are economically strong enough for the fish farming industry to be able to use probiotic exposures. However, when the dilution is 1:200 or 1:100 or dip concentrations of 1:10 it seems to be valuable to the industry for both disease prevention and for an increased growth rate.

It is clearly an indication that it may be more beneficial to apply the probiotics in the freshwater phase in the smolt plant a few weeks before sea launch, but the beneficial results are also clearly evident when applied at sea launch.

The probiotic bacteria seem to assist the fish in stabilizing the situation related to challenges from pathogenic bacteria and seem to support defence mechanisms like the various parts of the immune system. Among the factors that reveal this are the SGR estimations in the larger industrial trials.

One of the more surprising and strong examples in this application is the trial where a 30 min bath in the freshwater phase as parr reduces the mortality caused by classical winter ulcer 4 to 5 months later in brackish and salt water. There is in addition a clear growth rate stimulation 4 to 5 months later in the seawater. To be able to secure such strong results in the fish farming industry with probiotic applications it seems to be optimal to try to design protocols that employ and combine the most optimal combinations of parameters with impact on the effect of the probiotic bacteria on the salmon. This application demonstrates some of the most important factors that need to be adjusted for the various industrial adaptions needed for the exposure protocols.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

ASPECTS OF THE INVENTION

Aspect 1: A method for increasing the growth rate and/or weight of fish, said method comprising the steps of
 a) adding one or more species of probiotic bacteria to water, wherein the species of probiotic bacteria comprises or consists of *Aliivibrio njordis, Aliivibrio balderis* and/or *Aliivibrio nannie*; and
 b) exposing the fish to the water containing the one or more species of probiotic bacteria.

Aspect 2: A method for treating and/or preventing a microbial infection in fish, said method comprising the steps of
 a) adding one or more species of probiotic bacteria to water, wherein the species of probiotic bacteria comprises or consists of *Aliivibrio njordis, Aliivibrio balderis* and/or *Aliivibrio nannie*; and
 b) exposing the fish to the water containing the one or more species of probiotic bacteria.

Aspect 3: The method according to aspect 2, wherein the microbial infection is a bacterial infection.

Aspect 4: The method according to aspect 3, wherein the bacterial infection is an infection causing wounds, ulcers and/or lesions on the skin of the fish, and/or septicaemia.

Aspect 5: The method according to any one of aspects 3 and 4, wherein the bacterial infection is caused by one of more of a bacterium selected from the group comprising *M. viscose, Bizionia piscinecroseptica, Aliivibrio friggiae, Tenacibaculum dicentrarchi, Aliivibrio wodanis, Aliivibrio salmonicida, Aeromonas salmonicida, Vibrio anguillarum, Edwardsiella piscicida, Aeromonas hydrophila, Flavobacterium psychrophilum*, and *Aliivibrio* salmonicida.

Aspect 6: The method according to any one of the preceding aspects, wherein the water has a salt concentration of about 0 to about 4% by weight, such as about 2 to about 4.

Aspect 7: The method according to any one of the preceding aspects, wherein said water is natural sea water.

Aspect 8: The method of any one of the preceding aspects, wherein the fish are exposed to the species of probiotic bacteria for a time period of 1 second to 5 hours, such as 1 second to 2 hours, such as 1 second to 1 hour, such as 30 seconds to 1 hour or 1 minute to 30 minutes.

Aspect 9: The method according to any one of the preceding aspects, wherein the method is repeated one or more times, such as 1-20 times.

Aspect 10: The method of any one of the preceding aspects wherein said fish are fish of the family Salmonidae, such as salmon, trout, chars, freshwater whitefishes or graylings.

Aspect 11: The method according to any one of the preceding aspects, wherein said fish are farmed fish.

Aspect 12: A probiotic bacterium of the species *Aliivibrio njordis, Aliivibrio balderis* and/or *Aliivibrio nannie* for medical use.

Aspect 13: A probiotic bacterium of the species *Aliivibrio njordis, Aliivibrio balderis* and/or *Aliivibrio nannie* for use in the treatment and/or prevention of a microbial infection in fish.

Aspect 14: The probiotic bacterium of the species *Aliivibrio njordis, Aliivibrio balderis* and/or *Aliivibrio nannie* for use according to aspect 13, wherein the microbial infection is a bacterial infection.

Aspect 15: The probiotic bacterium of the species *Aliivibrio njordis, Aliivibrio balderis* and/or *Aliivibrio nannie* for use according to aspect 14, wherein the bacterial infection is an infection causing wounds, ulcers and/or lesions on the skin of the fish, and/or septicaemia.

Aspect 16: The probiotic bacterium of the species *Aliivibrio njordis, Aliivibrio balderis* and/or *Aliivibrio nannie* for use according to any one of aspects 13-15, wherein the bacterial infection is caused by one of more of a bacterium selected from the group comprising *M. viscose, Bizionia piscinecroseptica, Aliivibrio friggiae, Tenacibaculum dicentrarchi, Aliivibrio wodanis, Aliivibrio salmonicida, Aeromonas salmonicida, Vibrio anguillarum, Edwardsiella piscicida, Aeromonas hydrophila, Flavobacterium psychrophilum*, and *Aliivibrio* salmonicida.

Aspect 17: The probiotic bacterium of the species *Aliivibrio njordis, Aliivibrio balderis* and/or *Aliivibrio nannie* for use according to any one of aspects 13-16, wherein the probiotic bacterium is administered to the fish by
 a) adding one or more species of the probiotic bacterium to water; and
 b) exposing the fish to the water containing the one or more species of the probiotic bacterium.

Aspect 18: The probiotic bacterium of the species *Aliivibrio njordis, Aliivibrio balderis* and/or *Aliivibrio nannie* for use according to any one of aspects 13-17, wherein the water has a salt concentration of about 0 to about 4% by weight, such as about 2 to about 4.

Aspect 19: The probiotic bacterium of the species *Aliivibrio njordis, Aliivibrio balderis* and/or *Aliivibrio nannie* for use according to any one of aspects 13-18, wherein said water is natural sea water.

Aspect 20: The probiotic bacterium of the species *Aliivibrio njordis, Aliivibrio balderis* and/or *Aliivibrio nannie* for use according to any one of aspects 13-19, wherein the fish are exposed to the species of probiotic bacteria for a time period of 1 second to 5 hours, such as 1 second to 2 hours, such as 1 second to 1 hour, such as 30 seconds to 1 hour or 1 minute to 30 minutes.

Aspect 21: The probiotic bacterium of the species *Aliivibrio njordis, Aliivibrio balderis* and/or *Aliivibrio nannie* for use according to any one of aspects 13-20, wherein the fish are exposed to the species of probiotic bacteria one or more times, such as 1-20 times.

Aspect 22: The probiotic bacterium of the species *Aliivibrio njordis, Aliivibrio balderis* and/or *Aliivibrio nannie* for use according to any one of aspects 13-20, wherein said fish are fish of the family Salmonidae, such as salmon, trout, chars, freshwater whitefishes or graylings.

Aspect 23: The probiotic bacterium of the species *Aliivibrio njordis, Aliivibrio balderis* and/or *Aliivibrio nannie* for use according to any one of aspects 13-22, wherein said fish are farmed fish.

Aspect 24: A probiotic bacterium of the species *Aliivibrio njordis, Aliivibrio balderis* and/or *Aliivibrio nannie* for use in the treatment and/or prevention of a microbial infection in fish and for the simultaneous use in increasing the weight of said fish.

Aspect 25: A probiotic composition comprising one or more of a probiotic bacterium selected from the group consisting of *Aliivibrio njordis, Aliivibrio balderis* and *Aliivibrio nannie*.

Aspect 26: An isolated and biologically pure strain of *Aliivibrio njordis* strain B1-25, 18-1/2013 mandib V11, which has been deposited at National Collection of Industrial and Marine Bacteria and has been assigned accession number NCIMB 42593.

Aspect 27: An isolated and biologically pure strain of *Aliivibrio balderis* B1-24, 18-1/2013 kidn V12, which has been deposited at National Collection of Industrial and Marine Bacteria and has been assigned accession number NCIMB 42592.

Aspect 28: An isolated and biologically pure strain of *Aliivibrio nannie* B8-24, 313/2013 kidn V13, which has been deposited at National Collection of Industrial and Marine Bacteria and has been assigned accession number NCIMB 42594.

Aspect 30: Use of a probiotic bacterium of the species *Aliivibrio njordis, Aliivibrio balderis* and/or *Aliivibrio nannie* for the manufacture of a medicament for the treatment and/or prevention of a microbial infection in fish, such as a bacterial infection causing wounds, ulcers and/or lesions on the skin of the fish, and/or septicaemia, and simultaneously increasing the growth rate and/or weight of said fish.

Aspect 31: A method for the treatment and/or prevention of a microbial infection in fish and simultaneously increasing the growth rate and/or weight of fish, said method comprising the steps of
a) adding one or more species of probiotic bacteria to water, wherein the species of bacteria comprises or consists of *Aliivibrio njordis, Aliivibrio balderis* and/or *Aliivibrio nannie*; and
b) exposing the fish to the water containing the one or more species of probiotic bacteria.

REFERENCES

1. Toranzo, A. E., Magariños, B., Romalde, J. L. 2005. *A review of the main bacterial fish diseases in mariculture systems*. Aquaculture 246 (2005) 37-61.
2. Karlsen, C., Sørum, H., Willassen, N. P., Åsbakk, K. 2012. *Moritella viscosa* bypasses Atlantic salmon epidermal keratocyte clearing activity and might use skin surfaces as a port of infection. Vet Microbiol, 154(3-4):353-62. Epub 2011 Jul. 30.
3. Lunder, T., Evensen, Ø., Holstad, G., and Håstein, T. 1995. "Winter ulcer" in the Atlantic salmon Salmo salar. Pathological and bacteriological investigations and transmission experiments. Dis. Aquat. Org. 23: 39-49.
4. Løvoll, M., Wiik-Nielsen, C. R., Tunsjø, H. S., Colquhoun, D., Lunder, T., Sørum, H., Grove, S. 2009. Atlantic salmon bath challenged with *Moritella viscosa*—Pathogen invasion and host response. Fish Shellfish Immunol, 26: 877-884.
5. Cipriano, R. C. and R. A. Holt. 2005. *Flavobacterium psychrophilum*, cause of Bacterial Cold-Water Disease and Rainbow Trout Fry Syndrome. Fish Disease Leaflet No. 86. United States Dept. of the Interior. U.S. Geological Service, National Fish Health Research Laboratory, Kearneysville, W.V.
6. Nematollahi A, Decostere A, Pasmans F, Haesebrouck F. 2003. *Flavobacterium psychrophilum* infections in salmonid fish. J Fish Dis.; 26(10):563-74.
7. Verschuere, L, Rombaut, G, Sorgeloos, P., Verstraete, W. 2000. Probiotic bacteria as biological control agents in aquaculture. Microbiol. Mol. Biol. Rev. 64: 655-671.
8. Kashulin A. & Sørum H. 2014. *A* novel in vivo model for rapid evaluation of *Aliivibrio salmonicida* infectivity in Atlantic salmon. Aquaculture 420, 112-118.

The invention claimed is:

1. A method for increasing the weight and/or growth rate of fish, said method comprising the steps of
a) adding a solution comprising $10^4$ to $10^{12}$ CFUs of one or more species of probiotic bacteria to water in a tank comprising said fish, wherein the species of bacteria comprises *Aliivibrio njordis, Aliivibrio balderis* and/or *Aliivibrio nannie*; and
b) exposing the fish to the water containing the one or more species of probiotic bacteria.

2. The method of claim 1 wherein said fish are fish of the family Salmonidae.

3. The method of claim 1, wherein said exposing is for a time period of one second to five hours.

4. The method of claim 2, wherein said fish are selected from the group consisting of salmon, trout, chars, freshwater whitefishes and graylings.

5. The method of claim 1, wherein said one or more species of probiotic bacteria is *Aliivibrio njordis, Aliivibrio balderis* and *Aliivibrio nannie*.

6. The method of claim 1, wherein said *Aliivibrio njordis* is strain B1-25, 18-1/2013 mandib V11, which has been deposited at National Collection of Industrial and Marine Bacteria and has been assigned accession number NCIMB 42593.

7. The method of claim 1, wherein said *Aliivibrio balderis* is strain B1-24, 18-1/2013 kidn V12, which has been deposited at National Collection of Industrial and Marine Bacteria and has been assigned accession number NCIMB 42592.

8. The method of claim 1, wherein said *Aliivibrio nannie* is strain B8-24, 313/2013 kidn V13, which has been deposited at National Collection of Industrial and Marine Bacteria and has been assigned accession number NCIMB 42594.

* * * * *